United States Patent
Wiesner et al.

(10) Patent No.: US 12,115,231 B2
(45) Date of Patent: *Oct. 15, 2024

(54) ULTRASMALL NANOPARTICLES AND METHODS OF MAKING AND USING SAME

(71) Applicant: CORNELL UNIVERSITY, Ithaca, NY (US)

(72) Inventors: Ulrich B. Wiesner, Ithaca, NY (US); Kai Ma, Belle Mead, NJ (US); Carlie Mendoza, East Meadow, NY (US)

(73) Assignee: Cornell University, Ithaca, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/852,242

(22) Filed: Jun. 28, 2022

(65) Prior Publication Data
US 2023/0140770 A1 May 4, 2023

Related U.S. Application Data

(63) Continuation of application No. 17/676,364, filed on Feb. 21, 2022, now abandoned, which is a continuation of application No. 15/571,420, filed as application No. PCT/US2016/030752 on May 4, 2016, now Pat. No. 11,291,737.

(60) Provisional application No. 62/156,380, filed on May 4, 2015.

(51) Int. Cl.
| | | |
|---|---|---|
| A61K 49/00 | (2006.01) | |
| A61B 5/00 | (2006.01) | |
| A61K 9/14 | (2006.01) | |
| A61K 9/51 | (2006.01) | |
| A61P 35/00 | (2006.01) | |

(52) U.S. Cl.
CPC ........ *A61K 49/0093* (2013.01); *A61B 5/0071* (2013.01); *A61K 9/141* (2013.01); *A61K 9/5115* (2013.01); *A61K 9/5146* (2013.01); *A61K 9/5192* (2013.01); *A61K 49/0032* (2013.01); *A61P 35/00* (2018.01)

(58) Field of Classification Search
CPC .. A61K 9/0004; A61K 9/0034; A61K 9/2027; A61K 9/2031; A61K 9/2072; A61K 9/2095; A61K 31/165; A61K 31/167; A61K 9/2004; A61K 31/16; A61M 31/002; A61M 31/007; A61M 2202/06; B65B 1/16; A61P 13/10; A61P 23/00; A61P 23/02

See application file for complete search history.

(56) References Cited

U.S. PATENT DOCUMENTS

| | | |
|---|---|---|
| 2012/0223273 A1 | 9/2012 | Wiesner et al. |
| 2013/0039848 A1 | 2/2013 | Bradbury et al. |
| 2021/0030901 A1 | 2/2021 | Wiesner et al. |

FOREIGN PATENT DOCUMENTS

| | | | |
|---|---|---|---|
| CN | 102459062 A | 5/2012 | |
| JP | 2009220026 A | 10/2009 | |
| JP | 2012-524014 A | 10/2012 | |
| WO | 2009029870 A2 | 3/2009 | |
| WO | 2010/121064 A2 | 10/2010 | |
| WO | 2011/003109 A1 | 1/2011 | |
| WO | WO-2012051341 A1 * | 4/2012 | ......... A61K 49/0065 |
| WO | 2013/192609 A1 | 12/2013 | |
| WO | 2014/130643 A1 | 8/2014 | |

OTHER PUBLICATIONS

Benezra et al., Multimodal silica nanoparticles are effective cancer-target probes in a model of human melanoma, Journal of Clinical Investigation, vol. 121, No. 7, pp. 2768-2780 Jul. 1, 2011.
Lillo et al., Organic-coating of 1-2 nm size silicon nanoparticles: effect on particle properties, Nano Research, vol. 8, No. 6, pp. 2047-2062 Jan. 8, 2015.
Ma. K., et al., Controlling Growth of Ultrasmall Sub-10 nm Fluorescent Mesoporous Silica Nanoparticles, Chemistry of Materials, Feb. 11, 2013, vol. 25, pp. 677-691.
Ma et al., Controlling Growth of Ultrasmall Sub-10 nm Flourescent Mesoporous Silica Nanoparticles, Chemistry of Materials, vol. 25, No. 5, pp. 677-691 Mar. 12, 2015.
Ma, K., et al., Control of Ultrasmall Sub-10 nm Ligand-Functionalized Fluorescent Core-Shell Silica Nanoparticle Growth in Water, Chem. Mater., May 13, 2015, vol. 27, May 13, 2015, pp. 4119-4133.
Ma et al., Elucidating the Mechanism of Silica Nanoparticle PEGylation Processes Using Flourescence Correlation Spectroscopies, vol. 28, No. 5, pp. 1537-1545 Feb. 8, 2016.
Mendoza, Cornell Prime Dots (C' dots): Ultrasmall PEDylated Flourescent Core-Shell Silica Nanoparticles for Cancer rheranostics, pp. 1-28 May 1, 2016.
Poduval, D.G., On the Role of Acidity in Amorphous Silica-Alumina Based Catalysts, Eindhoven University of rechnology Library, Thesis, Apr. 5, 2011, 51 pages.
Rio-Echevarria et al., Highly PEGylated silica nanoparticles: "ready to use" stealth functional nanocarriers, Journal of Materials Chemistry, vol. 20, No. 14, pp. 2780 Jan. 1, 2010.

(Continued)

*Primary Examiner* — Robert S Cabral
(74) *Attorney, Agent, or Firm* — Hodgson Russ LLP

(57) ABSTRACT

An aqueous synthesis methodology for the preparation of silica nanoparticles (SNPs), core-shell SNPs having, for example, a size of 2 to 15 nm and narrow size-dispersion with size control below 1 nm, i.e. at the level of a single atomic layer. Different types of dyes, including near infrared (NIR) emitters, can be covalently encapsulated within and brightness can be enhanced via addition of extra silica shells. The surface may be functionalized with polyethylene glycol (PEG) groups and, optionally, specific surface ligands. This aqueous synthesis methodology also enables synthesis of 2 to 15 nm sized fluorescent core and core-shell aluminosilicate nanoparticles (ASNPs) which may also be surface functionalized. Encapsulation efficiency and brightness of highly negatively charged NIR fluorophores is enhanced relative to the corresponding SNPs without aluminum.

17 Claims, 24 Drawing Sheets

(56) References Cited

OTHER PUBLICATIONS

Stober, et al., "Controlled Growth of Monodisperse Silica Spheres in the Micron Size Range," Journal of Colloid and hterface Science, 26, (1968), all enclosed pages cited.
Fleischman, T. "Latest Cornell dot features a new cancer weapon: antibodies." Cornell Chronicle. [https://news.cornell.edu/stories/2018/10/latest-cornell-dot-features-new-cancer-weapon-antibodies]. Oct. 10, 2018.

* cited by examiner

ULTRASMALL NANOPARTICLES AND METHODS OF MAKING AND USING SAME

CROSS-REFERENCE TO RELATED APPLICATIONS

This application is a continuation of U.S. application Ser. No. 17/676,364 filed Feb. 21, 2022, which is a continuation of U.S. application Ser. No. 15/571,420 filed Nov. 2, 2017 (which issued on Apr. 5, 2022 as U.S. Pat. No. 11,291,737), which is a national phase entry of PCT/US2016/030752 filed May 4, 2016, which claims priority to U.S. provisional application No. 62/156,380, filed on May 4, 2015, the contents of each of the above-identified applications are hereby fully incorporated herein by reference in their entirety.

STATEMENT REGARDING FEDERALLY SPONSORED RESEARCH

This invention was made with government support under grant no. CA161280 awarded by the National Institutes of Health. The government has certain rights in the invention.

FIELD OF THE DISCLOSURE

The disclosure generally relates to ultrasmall nanoparticles and methods of making and using same. More particularly the disclosure generally relates to ultrasmall silica and aluminosilicate nanoparticles.

BACKGROUND OF THE DISCLOSURE

Silica nanoparticles (SNPs) have attracted interest for potential therapeutic/diagnostic applications due to their large surface-area, inertness and high bio-compatibility. However, most SNPs are >10 nm in size.

Particles>12 nm are not effectively cleared from the body in vivo and unfavorably distribute to the liver and other organs/tissues, potentially exposing these tissues to toxic elements (especially if these>10 nm SNPs are modified with drugs and/or radioactivity). Particles about 8 nm in diameter reside in the body for about a day, 10-11 nm about 3-5 days, but if greater than 12 nm do not clear or clear very slowly.

Currently, ultrasmall inorganic nanoparticles are of rapidly increasing interest as nanomedicines for cancer theranostics. Some organic based nanomedicines are already more competitive than conventional chemotherapy drugs due to multifunctionality and multivalency effects. Inorganic nanoparticles further diversify the building elements of nanomedicines and may provide advantages associated with their intrinsic physical properties and lower manufacturing costs. Safe translation of nanoparticles from the laboratory to the clinic requires overcoming a number of substantial scientific and regulatory hurdles. The most important criteria are favorable biodistribution and its time evolution (pharmacokinetics, PK) profiles. The size threshold for renal clearance is below 10 nm. Until today only a small number of inorganic nanoparticle platforms have been synthesized with sizes below 10 nm allowing for efficient renal clearance. Among those only<10 nm sized polyethylene glycol coated (PEGylated) fluorescent core-shell silica nanoparticles (SNPs) referred to as Cornell dots or simply C dots have been approved by the U.S. Food and Drug Administration (FDA) as an investigational new drug (IND) for first in-human clinical trials. Although the first clinical trial results with melanoma patients are encouraging, several synthesis challenges remain for such sub 10 nm sized fluorescent organic-inorganic hybrid SNPs.

First, all previous C dot-type SNP synthesis efforts followed a modified Stöber process in which alcohol was used as solvent. For materials for use in biological or clinical applications, however, water as a reaction medium would be preferred. It would greatly simplify synthesis and cleaning protocols leading to less volatile waste, thereby rendering particle production substantially faster and more cost effective. Furthermore, although the Stöber process is widely used to produce SNPs with diameters from tens of nm to microns, particle sizes of 10 nm and below are at the limit of size control of this synthesis process due to reaction kinetics limitations in alcohol.

Second, covalently covering silica particle surfaces with PEG can be tricky as the loss of surface charge during PEGylation may result in particle aggregation or at least broadening of the particle size distribution. This effect is more pronounced for ultrasmall particles due to the increase of particle surface energy, and thus limits the particle monodispersity and size control ability.

Third, as a result of the negative surface charge of silica above its isoelectric point at pH 2-3, covalent encapsulation efficiencies for silane-conjugated organic fluorescent dyes with negatively charged groups into SNPs are low as a result of electrostatic repulsion between silica and fluorophore. This is particularly true for near-infrared (NIR) emitting dyes most desirable for imaging applications in living tissue. NIR dyes have large delocalized 7C-electron systems and to be soluble in water typically require multiple negatively charged functional groups (e.g. sulfates) on their periphery. Low incorporation efficiencies are a problem for these dyes as their typical costs are of order $200-$300 per mg and re-use of typically employed silane-dye conjugates after the initial synthesis is problematic.

Finally, no inorganic elemental compositions other than silica have been reported for <10 nm sized fluorescent SNPs and core-shell SNPs. In particular, compositions are of interest leading to higher rigidity of the organic dye environments as increases in rigidity have directly been correlated with increases in per dye fluorescence yield as a result of decreases in non-radiative rates. Here silica compositions derived from aluminum alkoxides as additives are particularly interesting as they are known hardening components in alkoxysilane derived silica and alumina is an approved adjuvant added to high-volume vaccinations injected intramuscularly and subcutaneously.

All these challenges suggest revisiting the original fluorescent core-shell SNP (C dot) synthesis in order to systematically develop a water based approach to <10 nm organic-inorganic hybrid dots with improved size control, previously unknown compositions, and enhanced performance characteristics.

SUMMARY OF THE DISCLOSURE

An aqueous synthesis methodology for the preparation of narrowly size-dispersed fluorescent silica nanoparticles (SNPs) and core-shell SNPs with size control accuracy below 1 nm, i.e. at the level of a single atomic layer. Different types of fluorophores, including near infrared (NIR) emitters, can be covalently encapsulated. Brightness can be enhanced via addition of extra silica shells.

This methodology further enables synthesis of <10 nm sized fluorescent core and shell SNPs with previously unknown compositions. In particular addition of an aluminum sol-gel precursor leads to fluorescent aluminosilicate nanoparticles (ASNPs) and core-shell ASNPs. Encapsulation efficiency and brightness of highly negatively charged NIR fluorophores is enhanced relative to the corresponding SNPs without aluminum. Resulting particles show quantum yields of ~0.8, i.e. starting to approach the theoretical brightness limit.

All particles may be PEGylated providing steric stability. Heterobifunctional PEGs can be employed to introduce ligands onto the PEGylated particle surface of fluorescent SNPs, core-shell SNPs, and their aluminum containing analogues, producing ligand functionalized<10 nm NIR fluorescent nanoprobes. In order to distinguish the water based synthesis derived materials from earlier alcohol-based modified Stöber process derived fluorescent core-shell SNPs referred to as Cornell dots or C dots, the SNPs and ASNPs described here and synthesized in water will be referred to as Cornell prime dots or C' dots and AlC' dots.

These organic-inorganic hybrid nanomaterials may find applications in nanomedicine, including cancer diagnostics and therapy (theranostics).

By varying the synthesis conditions, C' dots and AlC' dots can range from about 2.4 nm to about 7.3 nm or greater. Conditions which may vary include: the temperature of the reaction; the concentration of TMOS or comparable compound; the concentration of base (e.g., ammonium hydroxide) and/or the particle growth period. Examples of these conditions are included in Table 1 of Example 1.

The temperature can range from about RT to about 80° C. or greater. The concentration of TMOS can range from about 0.011M to about 0.043M or greater. The concentration of ammonia hydroxide can range from about 0.002M to about 0.06M or greater. The particle growth period can range from about 10 minutes to about 20 hours or greater.

BRIEF DESCRIPTION OF THE FIGURES

For a fuller understanding of the nature and objects of the disclosure, reference should be made to the following detailed description taken in conjunction with the accompanying figures.

DETAILED DESCRIPTION OF THE DISCLOSURE

Figure 1:
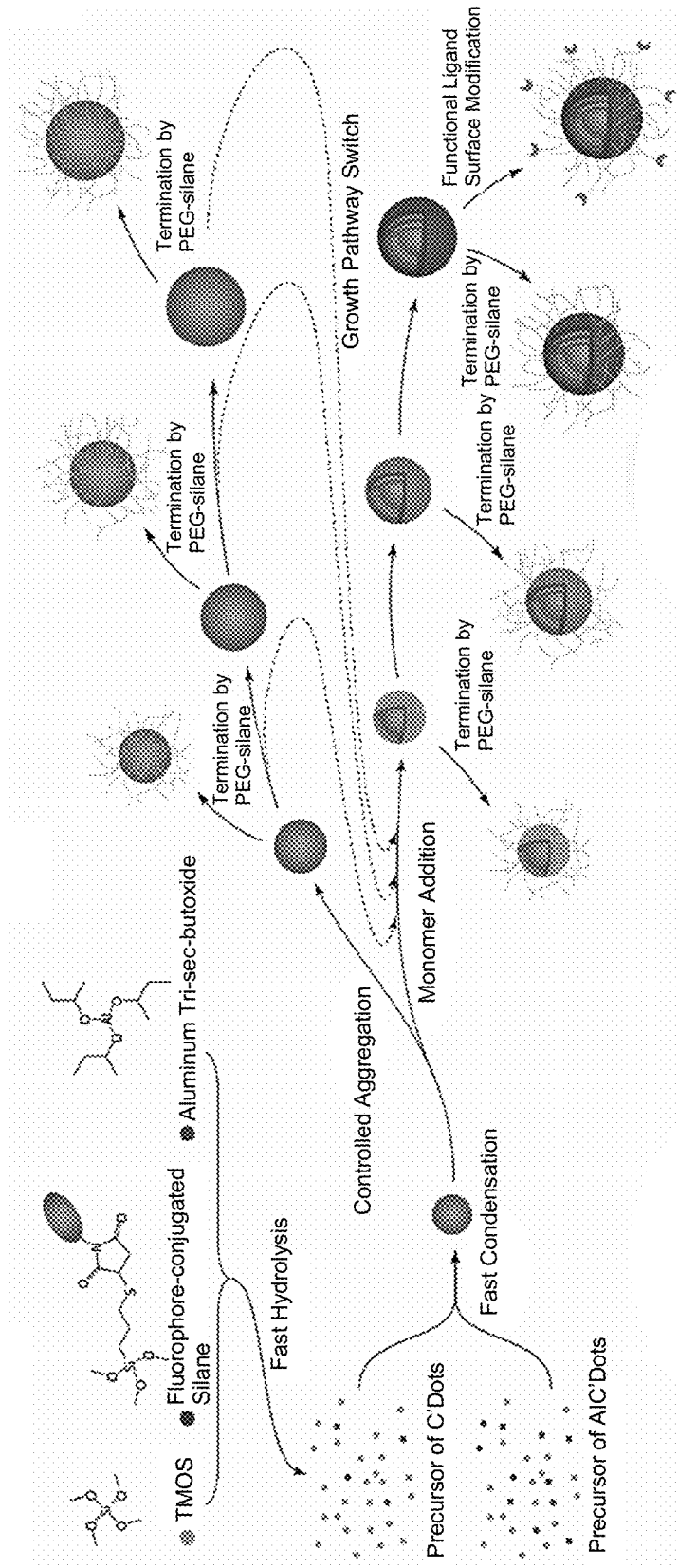
FIG. 1 is an illustration of water based fluorescent SNP growth pathways together with the chemical structures of produced particles.
Figure 1:
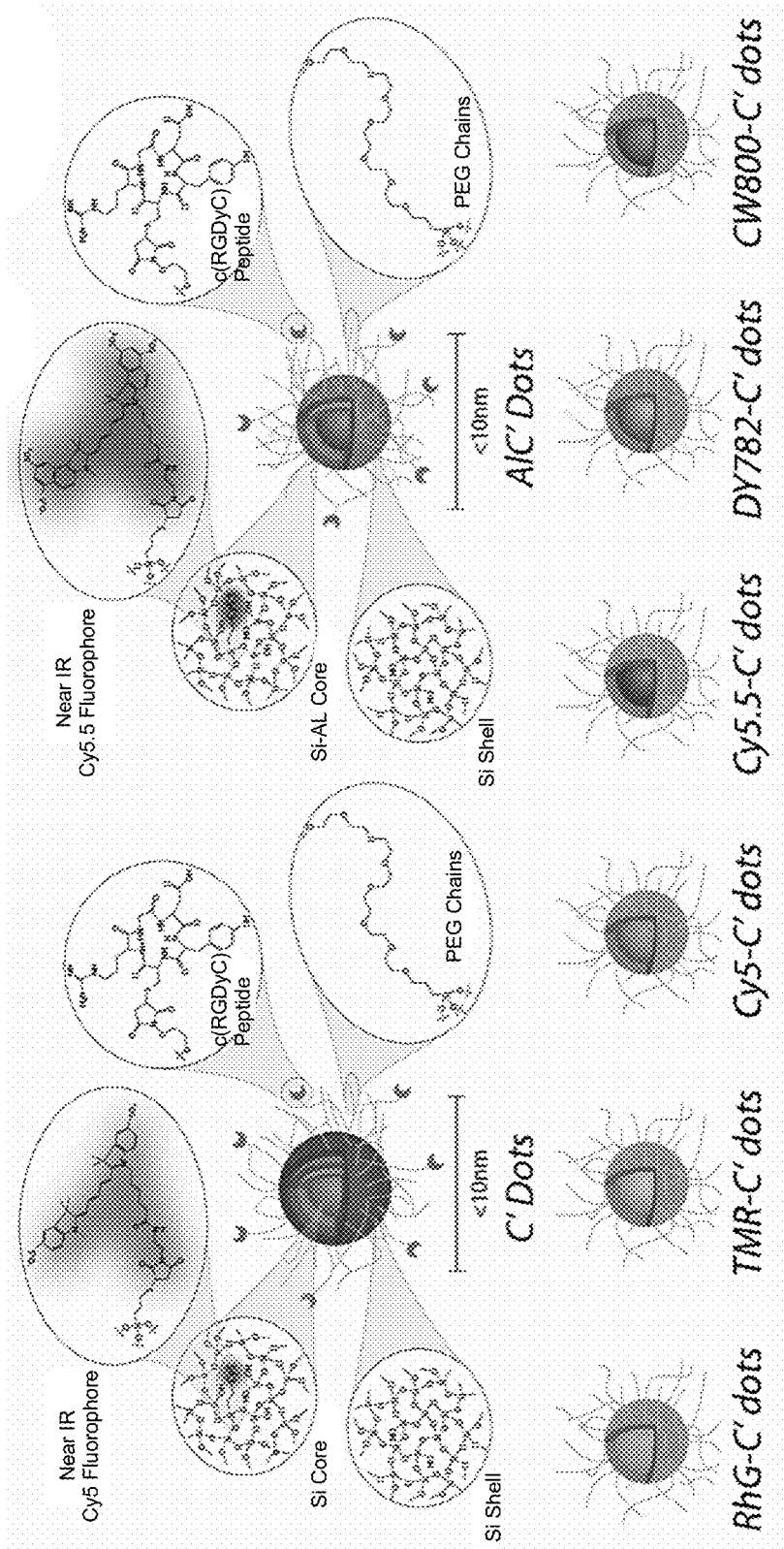

The present disclosure provides nanoparticles (e.g., core or core-shell nanoparticles). The nanoparticles are also referred to herein as ultrasmall nanoparticles. The present disclosure also provides methods of making and using the nanoparticles.

All ranges provided herein include all values that fall within the ranges to the tenth decimal place, unless indicated otherwise.

The techniques disclosed herein provide an aqueous synthesis approach to ultrasmall functional PEGylated fluorescent silica nanoparticles with improved control in multiple aspects, including particle size, particle size distribution, fluorescence wavelength, fluorescence brightness, compositions, particle PEGylation, particle surface functionalization, synthesis yield, product purity and manufacture reliability. The systematic and precise control covering all these aspects in a single organic-inorganic hybrid nanomaterials synthesis system has never been achieved before, preventing the safe translation of organic-inorganic hybrid nanomaterials from the laboratory to the clinic. Therefore, the techniques disclosed herein provide access to well-defined and systematically highly tunable silica-based nanomaterials that show significant potential in nanomedicine applications.

In an aspect, the present disclosure provides a method of making ultrasmall nanoparticles. The methods are based on use of aqueous reaction medium (e.g. water). The nanoparticles can be surface functionalized with polyethylene glycol groups (e.g., PEGylated).

The methods as described herein can be linearly scaled up, e.g., from 10 ml reaction to 1000 ml or greater without any substantial change in product quality. This scalability is important for large scale manufacture of the nanoparticles.

The methods are carried out in an aqueous reaction medium (e.g., water). For example, the aqueous medium comprises water. Certain reactants are added to the various reaction mixtures as solutions in a polar aprotic solvent (e.g., DMSO or DMF). In various examples, the aqueous medium does not contain organic solvents (e.g., alcohols such as $C_1$ to $C_6$ alcohols) other than polar aprotic solvents at 10% or greater, 20% or greater, or 30% or greater. In an example, the aqueous medium does not contain alcohols at 1% or greater, 2% or greater, 3% or greater, 4% or greater, or 5% or greater. In an example, the aqueous medium does not contain any detectable alcohols. For example, the reaction media of any of the steps of any of the methods disclosed herein consists essentially of water and, optionally, a polar aprotic solvent.

At various points in the methods the pH can be adjusted to a desired value or within a desired range. The pH the reaction mixture can be increased by addition of a base. Examples of suitable bases include ammonium hydroxide.

For example, a method of making nanoparticles or core-shell nanoparticles surface, which can be surface functionalized with polyethylene glycol groups (i.e., PEGylated) comprises: a) forming a reaction mixture at room temperature (e.g., 15° C. to 25° C. depending on the location) comprising water and TMOS (a silica core forming monomer) (e.g., at a concentration of 11 mM to 270 mM), wherein the pH of the reaction mixture (which can be adjusted using a base such as, for example, ammonium hydroxide) is 6 to 9 (which results in formation of core precursor nanoparticles having an average size (e.g., longest dimension) of, for example, 1 nm to 2 nm); b) either i) holding the reaction mixture at a time ($t^1$) and temperature ($T^1$) (e.g., ($t^1$) 0.5 days to 7 days at room temperature to 95° C. ($T^1$)), whereby nanoparticles (core nanoparticles) having an average size (e.g., longest dimension) of 2 to 15 nm are formed, or ii) cooling the reaction mixture to room temperature, if necessary, and adding a shell forming monomer (e.g., tetraethyl orthosilicates, other than TMOS, such as, for example, TEOS or TPOS) (the addition is carried out such that the shell forming monomer concentration is below the threshold for secondary nucleation) to the reaction mixture from a), whereby core-shell nanoparticles having an average size (e.g., longest dimension) of 2 to 50 nm (e.g., 2 to 15 nm) are formed; c) adjusting, if necessary, the pH of the reaction mixture to a pH of 6 to 10 comprising the core nanoparticles or core-shell nanoparticles from b) i) or b) ii), respectively; and d) optionally (PEGylating the core nanoparticles or core-shell nanoparticles by) adding at room temperature to the reaction mixture comprising the core nanoparticles or core-shell nanoparticles from b) i) or b) ii), respectively, a PEG-silane conjugate (comprising a PEG moiety covalently bound to a silane moiety) (e.g., at a concentration of 10 mM to 60 mM) (e.g., PEG-silane conjugate dissolved in a polar aprotic solvent such as, for example, DMSO or DMF) and holding the resulting reaction mixture at a time ($t^2$) and temperature ($T^2$) (e.g., ($t^2$) 0.5 minutes to 24 hours at room temperature ($T^2$)) (whereby at least a portion of the PEG-silane conjugate molecules are adsorbed on at least a portion of the surface of the core nanoparticles or core-shell nanoparticles from b)); e) heating the mixture from d) at a time ($t^3$) and temperature ($T^3$) (e.g., ($t^3$) 1 hour to 24 hours at 40° C. to 100° C. ($T^3$)), whereby the nanoparticles surface functionalized with polyethylene glycol groups or the core-shell nanoparticles surface functionalized with polyethylene glycol groups are formed.

The nanoparticles can be subjected to post-synthesis processing steps. For example, after synthesis (e.g., after e) in the example above) the solution is cooled to room temperature and then transferred into a dialysis membrane tube (e.g. a dialysis membrane tube having a Molecular Weight Cut off 10,000, which are commercially available (e.g., from Pierce)). The solution in the dialysis tube is dialyzed in DI-water (volume of water is 200 times more than the reaction volume, e.g. 2000 ml water for a 10 ml reaction) and the water is changed every day for one to six days to wash away remaining reagents, e.g. ammonium hydroxide and free silane molecules. The particles are then filtered through a 200 nm syringe filter (fisher brand) to remove aggregates or dust. If desired, additional purification processes, including gel permeation chromatography and high-performance liquid chromatography, can be applied to the nanoparticles to further ensure the high purify of the synthesized particles (e.g., 1% or less unreacted reagents or aggregates). After any purification processes, the purified nanoparticles can be transferred back to deionized water if other solvent is used in the additional processes.

The cores can be silicon cores. The reaction mixture used in silicon core formation can comprise TMOS as the only silicon core forming monomer.

The cores can be aluminosilicate cores. The reaction mixture used in aluminosilicate core formation can comprise TMOS as the only silicon core forming monomer and one or more alumina core forming monomer (e.g., an aluminum alkoxide such as, for example, aluminum-tri-sec-butoxide or a combination of aluminum alkoxides).

In the case of aluminosilicate core synthesis, the pH of the reaction mixture is adjusted to a pH of 1 to 2 prior to addition of the alumina core forming monomer. After aluminosilicate core formation, the pH of the solution is adjusted to a pH of 7 to 9 and, optionally, PEG with molecular weight between 100 and 1,000 g/mol, including all integer values and ranges therebetween, at concentration of 10 mM to 75 mM, including all integer mM values and ranges therebetween, is added to the reaction mixture prior to adjusting the pH of the reaction mixture to a pH of 7 to 9.

The reaction mixture used to form core nanoparticles can also comprise a dye precursor. In this case, the resulting core or core-shell nanoparticles have one or more dye molecules encapsulated or incorporated therein. For example, core nanoparticle has 1, 2, 3, 4, 5, 6, or 7 dye molecules encapsulated therein. Mixtures of dye precursors can be used. The dye precursor is a dye conjugated to a silane. For example, a dye with maleimido functionality is conjugated to thiol-functionalized silane. In another example, a dye with NHS ester functionality is conjugated to amine-functionalized silane. Examples of suitable silanes and conjugation chemistries are known in the art. The dye can have an emission (e.g., fluorescence) wavelength of 400 nm (blue) to 800 nm (near-infrared). For example, the dye is a NIR-dye. Examples of suitable dyes include, but are not limited to, rhodamine green (RHG), tetramethylrhodamine (TMR), Cyanine 5 (Cy5), Cyanine 5.5 (Cy5.5), Cyanine 7 (Cy7), ATTO647N, Dyomics DY800, Dyomics DY782 and IRDye 800CW, and the nanoparticles surface functionalized with polyethylene glycol groups or the core-shell nanoparticles surface functionalized with polyethylene glycol groups have one or more fluorescent dye molecules encapsulated therein.

A silica shell can be formed on the core nanoparticles. The silica shell is formed after, for example, core formation is complete. Examples of silica shell forming precursors include tetraalkylorthosilicates such as, for example, TEOS and TPOS. Mixtures of silica shell forming precursors can be used. TMOS is not a silica shell forming precursor. The silica shell forming precursor can be added to the reaction mixture as a solution in a polar aprotic solvent. Examples, of suitable polar aprotic solvents include DMSO and DMF.

It is desirable to add the silica shell forming precursors in separate aliquots. For example the shell forming monomer(s) is/are added in separate aliquots (e.g., 40 to 500 aliquots) The aliquots can include one or more shell forming precursor (e.g., TEOS and/or TPOS) and a polar aprotic solvent e.g., DMSO. Each aliquot can have 1 to 20 micromoles of shell forming monomer. The interval between aliquot addition can be 1 to 60 minutes, including all integer minute values and ranges therebetween. The pH of the reaction mixture can vary during the silica shell forming process. It is desirable to adjust the pH to maintain a pH of 7-8.

After core or core-shell nanoparticle formation, the core or core-shell nanoparticles can by reacted with one or more PEG-silane conjugates. Various PEG-silane conjugates can be added together or in various orders. This process is also referred to herein as PEGylation. The conversion percentage of PEG-silane is between 5% and 40% and the polyethylene glycol surface density is 1.3 to 2.1 polyethylene glycol molecules per $nm^2$. The conversion percentage of ligand-functionalized PEG-silane is 40% to 100% and the number of ligand-functionalized PEG-silane precursors reacted with each particle is 3 to 90.

PEGylation can be carried out at a variety of times and temperatures. For example, in the case of silica core or core-shell nanoparticles, PEGylation can be carried out by contacting the nanoparticles at room temperature for 0.5 minutes to 24 hours (e.g., overnight). For example, in the case of alumina-silicate nanoparticles (e.g., alumina-silicate core nanoparticles or silica core silica shell nanoparticles) the temperature is 80° C. overnight.

The chain length of the PEG moiety of the PEG-silane (i.e., the molecular weight of the PEG moiety) can be tuned from 3 to 24 ethylene glycol monomers (e.g., 3 to 6, 3 to 9, 6 to 9, 8 to 12, or 8 to 24 ethylene glycol monomers). The PEG chain length of PEG-silane can be selected to tune the thickness of the PEG layer surrounding the particle and the pharmaceutical kinetics profiles of the PEGylated particles. The PEG chain length of ligand-functionalized PEG-silane can be used to tune the accessibility of the ligand groups on the surface of the PEG layer of the particles resulting in varying binding and targeting performance.

PEG-silane conjugates can comprise a ligand. The ligand is covalently bound to the PEG moiety of the PEG-silane conjugates (e.g., via though the hydroxy terminus of the PEG-silane conjugates). The ligand can be conjugated to a terminus of the PEG moiety opposite the terminus conjugated to the silane moiety. The PEG-silane conjugate can be formed using a heterobifunctional PEG compound (e.g., maleimido-functionalized heterobifunctional PEGs, NHS ester-functionalized heterobifunctional PEGs, amine-functionalized heterobifunctional PEGs, thiol-functionalized heterobifunctional PEGs, etc.).

Examples of suitable ligands include, but are not limited to, peptides (natural or synthetic), ligands comprising a radio label (e.g., $^{124}I$, $^{131}I$, $^{225}Ac$ or $^{177}Lu$), antibodies, ligands comprising a reactive group (e.g., a reactive group that can be conjugated to a molecule such a drug molecule, gefitinib, etc.).

For example, PEG-silane conjugate comprising a ligand is added in addition to PEG-silane (e.g., in d) in the example above). In this case, nanoparticles surface functionalized with polyethylene glycol groups and polyethylene groups comprising a ligand or core-shell nanoparticles surface functionalized with polyethylene glycol groups and polyethylene groups comprising a ligand are formed. The conversion percentage of ligand-functionalized or reactive group-functionalized PEG-silane is 40% to 100% and the number of ligand-functionalized PEG-silane precursors reacted with each particle is 3 to 600.

For example, before or after (e.g., 20 seconds to 5 minutes before or after) the PEG-silane conjugate is added (e.g., in d) in the example above) a PEG-silane conjugate comprising a ligand (e.g., at concentration between 0.05 mM and 2.5 mM) is added at room temperature to the reaction mixture comprising the core nanoparticles or core-shell nanoparticles (e.g., from b) i) or b) ii), respectively, in the example above). The resulting reaction mixture is held at a time ($t^4$) and temperature ($T^4$) (e.g., ($t^4$) 0.5 minutes to 24 hours at room temperature ($T^4$)), where at least a portion of the PEG-silane conjugate molecules are adsorbed on at least a portion of the surface of the core nanoparticles or core-shell nanoparticles (e.g., from b) in the example above). Subsequently, the reaction mixture is heated at a time ($t^5$) and temperature ($T^5$) (e.g., ($t^5$) 1 hour to 24 hours at 40° C. to 100° C. ($T^5$)), where nanoparticles surface functionalized with polyethylene glycol groups comprising a ligand or core-shell nanoparticles surface functionalized with polyethylene glycol groups comprising a ligand are formed. Optionally, subsequently adding at room temperature to the resulting reaction mixture comprising nanoparticles surface functionalized with polyethylene glycol groups comprising a ligand or core-shell nanoparticles surface functionalized with polyethylene glycol groups comprising a ligand a PEG-silane conjugate (the concentration of PEG-silane no ligand is between 10 mM and 75 mM) (e.g., PEG-silane conjugate dissolved in a polar aprotic solvent such as, for example, DMSO or DMF), holding the resulting reaction mixture at a time ($t^6$) and temperature ($T^6$) (e.g., ($t^6$) 0.5 minutes to 24 hours at room temperature ($T^6$)) (whereby at least a portion of the PEG-silane conjugate molecules are adsorbed on at least a portion of the surface of the nanoparticles surface functionalized with polyethylene glycol groups comprising a ligand or at least a portion of the core-shell nanoparticles surface functionalized with polyethylene glycol groups comprising a ligand a PEG-silane conjugate, and heating the resulting mixture from at a time ($t^7$) and temperature ($T^7$) (e.g., ($t^7$) 1 hour to 24 hours at 40° C. to 100° C. ($T^7$)), whereby nanoparticles surface functionalized with polyethylene glycol groups and polyethylene glycol groups comprising a ligand or core-shell nanoparticles surface functionalized with polyethylene glycol groups and polyethylene groups comprising a ligand are formed.

In another example, at least a portion of or all of the PEG-silane has a reactive group on a terminus of the PEG moiety opposite the terminus conjugated to the silane moiety of the PEG-silane conjugate (is formed from a heterobifunctional PEG compound) and after formation of the nanoparticles surface functionalized with polyethylene glycol groups having a reactive group, and, optionally, polyethylene glycol groups, core-shell nanoparticles surface functionalized with polyethylene glycol groups having a reactive group. Optionally, polyethylene glycol groups are reacted with a second ligand (which can be the same or different than the ligand of the nanoparticles surface functionalized with polyethylene glycol groups and polyethylene glycol group comprising a ligand or the core-shell nanoparticles surface functionalized with polyethylene glycol groups and polyethylene groups comprising a ligand) functionalized with a second reactive group (which can be the same or different than the reactive group of the nanoparticles surface functionalized with polyethylene glycol groups and polyethylene glycol group comprising a ligand or the core-shell nanoparticles surface functionalized with polyethylene glycol groups and polyethylene groups comprising a ligand) thereby forming nanoparticles surface functionalized with polyethylene groups functionalized with a second ligand and, optionally, polyethylene glycol groups, core-shell nanoparticles surface functionalized with polyethylene groups functionalized with a second ligand and polyethylene glycol groups and, optionally, polyethylene glycol groups.

In another example, at least a portion of or all of the PEG-silane has a reactive group on a terminus of the PEG moiety opposite the terminus conjugated to the silane moiety of the PEG-silane conjugate (is formed from a heterobifunctional PEG compound) and after formation of the nanoparticles surface functionalized with polyethylene glycol groups and, optionally having a reactive group, and, optionally, polyethylene glycol groups, core-shell nanoparticles surface functionalized with polyethylene glycol groups having a reactive group, and, optionally, polyethylene glycol groups, are reacted with a second ligand (which can be the same or different than the ligand of the nanoparticles surface functionalized with polyethylene glycol groups and polyethylene glycol group comprising a ligand or the core-shell nanoparticles surface functionalized with polyethylene glycol groups and polyethylene groups comprising a ligand) functionalized with a second reactive group (which can be the same or different than the reactive group of the nanoparticles surface functionalized with polyethylene glycol groups and polyethylene glycol group comprising a ligand or the core-shell nanoparticles surface functionalized with polyethylene glycol groups and polyethylene groups comprising a ligand) thereby forming nanoparticles surface functionalized with polyethylene groups functionalized with a second ligand and, optionally, polyethylene glycol groups, core-shell nanoparticles surface functionalized with polyethylene groups functionalized with a second ligand and polyethylene glycol groups and, optionally, polyethylene glycol groups, where at least a portion of the PEG-silane has a reactive group on a terminus of the PEG moiety opposite the terminus conjugated to the silane moiety of the PEG-silane conjugate (is formed from a heterobifunctional PEG compound) and after formation of the nanoparticles surface functionalized with polyethylene glycol groups having a reactive group, core-shell nanoparticles surface functionalized with polyethylene glycol groups having a reactive group, nanoparticles surface functionalized with polyethylene glycol groups having a reactive group and polyethylene glycol groups comprising a ligand, or core-shell nanoparticles surface functionalized with polyethylene glycol groups having a reactive group and polyethylene groups comprising a ligand the reactive group are reacted with a second ligand functionalized with a reactive group (which can be the same or different than the ligand of the nanoparticles surface functionalized with polyethylene glycol groups and polyethylene glycol group comprising a ligand, or core-shell nanoparticles surface functionalized with polyethylene glycol groups and polyethylene groups comprising a ligand) thereby forming nanoparticles surface functionalized with polyethylene glycol groups and polyethylene groups functionalized with a second ligand, core-shell nanoparticles surface functionalized with polyethylene glycol groups and polyethylene groups functionalized with a second ligand, nanoparticles surface functionalized with polyethylene glycol groups comprising a ligand, or core-shell nanoparticles surface functionalized with polyethylene glycol groups and polyethylene groups comprising a ligand that is functionalized with the second ligand.

The nanoparticles with PEG groups functionalized with reactive groups can be further functionalized with one or more ligands. For example, a functionalized ligand can be reacted with a reactive group of a PEG group. Examples of suitable reaction chemistries and conditions for post-nanoparticle synthesis functionalization are known in the art.

The nanoparticles can have a narrow size distribution. In various examples, the nanoparticle size distribution (before or after PEGylation), not including extraneous materials such as, for example, unreacted reagents, dust particles/aggregates, is +/−5, 10, 15, or 20% of the average particle size (e.g., longest dimension). The particle size can be determined by methods known in the art. For example, the particle size is determined by TEM, GPS, or DLS. DLS contains systematic deviation and, therefore, the DLS size distribution may not correlate with the size distribution determined by TEM or GPS.

In an aspect, the present disclosure provides compositions comprising nanoparticles of the present disclosure. The compositions can comprise one or more types (e.g., having different average size and/or one or more different compositional feature).

For example, a composition comprises a plurality of core and/or core-shell nanoparticles (e.g., silica core nanoparticles, silica core-shell nanoparticles, aluminosilicate core nanoparticles, aluminosilicate core-shell nanoparticles. Any of the nanoparticles may be surface functionalized with one or more type of polyethylene glycol groups (e.g., polyethylene glycol groups, functionalized (e.g., functionalized with one or more ligand and/or a reactive group) polyethylene glycol groups, or a combination thereof). Any of the nanoparticles can have a dye or combination of dyes (e.g., a NIR dye) encapsulated therein. The dye molecules are covalently bound to the nanoparticles. The nanoparticles can be made by a method of the present disclosure.

The nanoparticles in a composition can have a variety of sizes. The nanoparticles can have a core size of 2 to 15 nm, including all 0.1 nm values and ranges therebetween. In various examples, the nanoparticles have a core size of 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, or 15 nm. In various examples, at least 90%, 95%, 96%, 97%, 98%, 99%, 99.5% 99.9%, or 100% of the core and/or core-shell nanoparticles have a size (e.g., longest dimension) of 2 to 15 nm. In various examples, at least 90%, 95%, 96%, 97%, 98%, 99%, 99.5% 99.9%, or 100% of the core-shell nanoparticles have a size (e.g., longest dimension) of 2 to 50 nm. In various examples, at least 90%, 95%, 96%, 97%, 98%, 99%, 99.5%, 99.9%, or 100% of the core and/or core of the core-shell nanoparticles have a size (e.g., longest dimension) of 2 to 15 nm. For the exemplary size distributions, the composition may not be subjected to any particle-size discriminating (particle size selection/removal) processes (e.g., filtration, dialysis, chromatography (e.g., GPC), centrifugation, etc.). For example, the nanoparticles of the present disclosure are the only nanoparticles in the composition.

The composition can comprise additional components. For example, the composition can also comprise a buffer suitable for administration to an individual (e.g., a mammal such as, for example, a human). The buffer may be a pharmaceutically-acceptable carrier.

The compositions, as synthesized and before any post-synthesis processing/treatment, can have nanoparticles, particles (2-15 nm), dust particles/aggregates (>20 nm), unreacted reagents (<2 nm).

In an aspect, the present disclosure provides uses of the nanoparticles and compositions of the present disclosure. For example, nanoparticles or a composition comprising the nanoparticles are used in delivery and/or imaging methods.

The ligands carried by the nanoparticles can include diagnostic and/or therapeutic agents (e.g., drugs). Examples of therapeutic agents include, but are not limited to, chemotherapeutic agents, antibiotics, antifungal agents, antiparasitic agents, antiviral agents, and combinations thereof. An affinity ligand may be also be conjugated to the nanoparticle to allow targeted delivery of the nanoparticles. For example, the nanoparticle may be conjugated to a ligand which is capable of binding to a cellular component (e.g., on the cell membrane or in the intracellular compartment) associated with a specific cell type. The targeted molecule can be a tumor marker or a molecule in a signaling pathway. The ligand can have specific binding affinity to certain cell types, such as, for example, tumor cells. In certain examples, the ligand may be used for guiding the nanoparticles to specific areas, such as, for example, liver, spleen, brain or the like. Imaging can be used to determine the location of the nanoparticles in an individual.

The nanoparticles or compositions comprising nanoparticles can be administered to individuals for example, in pharmaceutically-acceptable carriers, which facilitate transporting the nanoparticles from one organ or portion of the body to another organ or portion of the body. Examples of individuals include animals such as human and non-human animals. Examples of individuals also include mammals.

Pharmaceutically acceptable carriers are generally aqueous based. Some examples of materials which can be used in pharmaceutically-acceptable carriers include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. (See REMINGTON'S PHARM. SCI., 15th Ed. (Mack Publ. Co., Easton (1975)).

Compositions comprising the present nanoparticles can be administered to an individual by any suitable route—either alone or as in combination with other agents. Administration can be accomplished by any means, such as, for example, by parenteral, mucosal, pulmonary, topical, catheter-based, or oral means of delivery. Parenteral delivery can include, for example, subcutaneous, intravenous, intramuscular, intra-arterial, and injection into the tissue of an organ. Mucosal delivery can include, for example, intranasal delivery. Pulmonary delivery can include inhalation of the agent. Catheter-based delivery can include delivery by iontophoretic catheter-based delivery. Oral delivery can include delivery of an enteric coated pill, or administration of a liquid by mouth. Transdermal delivery can include delivery via the use of dermal patches.

Following administration of a composition comprising the present nanoparticles, the path, location, and clearance of the NPs can be monitored using one or more imaging techniques. Examples of suitable imaging techniques include Artemis Fluorescence Camera System.

This disclosure provides a method for imaging biological material such as cells, extracellular components, or tissues comprising contacting the biological material with nanoparticles comprising one or more dyes, or compositions comprising the nanoparticles; directing excitation electromagnetic (e/m) radiation, such as light, on to the tissues or cells thereby exciting the dye molecules; detecting e/m radiation emitted by the excited dye molecules; and capturing and processing the detected e/m radiation to provide one or more images of the biological material. One or more of these steps can be carried out in vitro or in vivo. For example, the cells or tissues can be present in an individual or can be present in culture. Exposure of cells or tissues to e/m radiation can be effected in vitro (e.g., under culture conditions) or can be effected in vivo. For directing e/m radiation at cells, extracellular materials, tissues, organs and the like within an individual or any portion of an individual's body that are not easily accessible, fiber optical instruments can be used.

For example, a method for imaging of a region within an individual comprises (a) administering to the individual nanoparticles or a composition of the present disclosure comprising one or more dye molecules; (b) directing excitation light into the subject, thereby exciting at least one of the one or more dye molecules; (c) detecting excited light, the detected light having been emitted by said dye molecules in the individuals as a result of excitation by the excitation light; and (d) processing signals corresponding to the detected light to provide one or more images (e.g. a real-time video stream) of the region within the subject.

Since the fluorescent particles are brighter than free dye, fluorescent particles can be used for tissue imaging, as well as to image the metastasis tumor. Additionally or alternatively, radioisotopes can be further attached to the ligand groups (e.g., tyrosine residue or chelator) of the ligand-functionalized particles or to the silica matrix of the PEGylated particles without specific ligand functionalization for photoinduced electron transfer imaging. If the radioisotopes are chosen to be therapeutic, such as $^{225}$Ac or $^{177}$Lu, this in turn would result in particles with additional radiotherapeutic properties.

For example, drug-linker conjugate, where the linker group can be specifically cleaved by enzyme or acid condition in tumor for drug release, can be covalently attached to the functional ligands on the particles for drug delivery. For example, drug-linker-thiol conjugates can be attached to maleimido-PEG-particles through thiol-maleimido conjugation reaction post the synthesis of maleimido-PEG-particles. Additionally, both drug-linker conjugate and cancer targeting peptides can be attached to the particle surface for drug delivery specifically to tumor.

The steps of the method described in the various embodiments and examples disclosed herein are sufficient to carry out the methods and produce the compositions of the present disclosure. Thus, in an embodiment, the method consists essentially of a combination of the steps of the methods disclosed herein. In another embodiment, the method consists of such steps.

In the following Statements, various examples of the methods and compositions of the present disclosure are described:

1. A method of making nanoparticles optionally surface functionalized with polyethylene glycol (PEG) groups (i.e., PEGylated), or core-shell nanoparticles optionally surface functionalized with PEG groups, comprising a) forming a reaction mixture at room temperature (e.g., 15° C. to 25° C. depending on the location) comprising water and TMOS (a silica core forming monomer) (e.g., at a concentration of 11 mM to 270 mM), wherein the pH of the reaction mixture (which can be adjusted using a base such as, for example, ammonium hydroxide) is 6 to 9 (which results in formation of core precursor nanoparticles having an average size (e.g., longest dimension) of, for example, 1 nm to 2 nm); b) either i) holding the reaction mixture at a time ($t^1$) and temperature ($T^1$) (e.g., ($t^1$) 0.1 hour to 7 days at room temperature to 95° C. ($T^1$), such as 10-15 minutes), whereby nanoparticles (core nanoparticles) having an average size (e.g., longest dimension) of 2 to 15 nm are formed, or ii) cooling the reaction mixture to room temperature, if necessary, and adding a shell forming monomer (e.g., tetraethyl orthosilicates, other than TMOS, such as, for example, TEOS or TPOS) (the addition is carried out such that the shell forming monomer concentration is below the threshold for secondary nucleation) to the reaction mixture from a), whereby core-shell nanoparticles having a core size (e.g., longest dimension) of 2 to 15 nm and/or an average size (e.g., longest dimension) of 2 to 50 nm are formed; c) adjusting, if necessary, the pH of the reaction mixture to a pH of 6 to 10 comprising the core nanoparticles or core-shell nanoparticles from b) i) or b) ii), respectively; and d) optionally (PEGylating the core nanoparticles or core-shell nanoparticles by) adding at room temperature to the reaction mixture comprising the core nanoparticles or core-shell nanoparticles from b) i) or b) ii), respectively, a PEG-silane conjugate (comprising a PEG moiety covalently bound to a silane moiety) (e.g., at a concentration of 10 mM to 60 mM) (e.g., if necessary, PEG-silane conjugate dissolved in a polar aprotic solvent such as, for example, DMSO or DMF) and holding the resulting reaction mixture at a time ($t^2$) and temperature ($T^2$) (e.g., ($t^2$) 0.5 minutes to 24 hours at room temperature ($T^2$)) (whereby at least a portion of the PEG-silane conjugate molecules are adsorbed on at least a portion of the surface of the core nanoparticles or core-shell nanoparticles from b)); e) optionally heating the mixture from d) at a time ($t^3$) and temperature ($T^3$) (e.g., ($t^3$) 1 hour to 24 hours at 40° C. to 100° C. ($T^3$)), whereby the nanoparticles surface functionalized with PEG groups or the core-shell nanoparticles surface functionalized with PEG groups are formed.

2. A method of Statement 1, wherein the reaction mixture further comprises alumina or aluminasilicate core forming monomer (e.g., aluminum alkoxides such as, for example, aluminum-tri-sec-butoxide) and the pH of the reaction mixture is adjusted to a pH of 1 to 2 prior to addition of the alumina or aluminasilicate core forming monomer and, optionally, PEG (e.g., PEG with molecular weight between 0.1 k and 1 k and concentration between 10 mM and 75 mM is added to the reaction mixture prior to adjusting the pH to a pH of 7 to 9, and the core is an aluminosilicate core.

3. A method of one of Statements 1 or 2, where in the reaction mixture further comprises a dye precursor (e.g., a silane-dye conjugate such as a silane-NIR dye conjugate) and the nanoparticles surface functionalized with PEG groups or the core-shell nanoparticles surface functionalized with PEG groups have one or more fluorescent dye molecules covalently encapsulated therein.

4. A method of Statement 3, wherein 1 to 7 (an average of 1 to 7, e.g., 2) dye molecules (e.g., fluorescent dye molecules such as, for example, NIR dye molecules) are present in each of the nanoparticles surface functionalized with PEG groups or core-shell nanoparticles surface functionalized with PEG groups.

5. A method of Statement 4, wherein the core is an aluminosilicate core and the number of dye molecules (e.g., fluorescent dye molecules such as, for example, NIR dye molecules) per particle is 1 to 7 (an average of 1 to 7, e.g., 2).

6. A method of any one of the preceding Statements, where in b) ii) the shell forming monomer is added in separate aliquots (e.g., 40 to 500 separate aliquots of, for example, a mixture of TEOS or TPOS and polar aprotic solvent e.g. DMSO, where the molar amount of shell forming monomer in each aliquot is between 2 and 20 micromoles, separated by 1 to 60 minutes) and, if necessary, adjusting the pH periodically to maintain a pH of 7-8.

7. A method of any one of the preceding Statements, where the PEG-silane conjugate comprises a ligand (e.g., a peptide (natural or synthetic), a ligand comprising a moiety comprising a radio label (e.g., $^{124}$I, $^{131}$I, $^{225}$Ac or $^{177}$Lu), antibody, a ligand comprising a reactive group (e.g., a reactive group that can be conjugated to a molecule such a drug molecule, e.g.) conjugated to a terminus of the PEG moiety opposite the terminus conjugated to the silane moiety (can be formed using a heterobifunctional PEG compound).

8. A method of any one of the preceding Statements, where PEG-silane conjugate comprising a ligand is added in addition to PEG-silane in d), whereby nanoparticles surface functionalized with PEG groups and polyethylene groups comprising a ligand or core-shell nanoparticles surface functionalized with PEG groups and polyethylene groups comprising a ligand are formed.

9. A method of any one of the preceding Statements, where before or after the PEG-silane conjugate is added in d) a PEG-silane conjugate comprising a ligand (e.g., at concentration between 0.05 mM and 2.5 mM) (e.g., PEG-silane conjugate comprising a ligand dissolved in a polar aprotic solvent such as, for example, DMSO or DMF) is added at room temperature to the reaction mixture comprising the core nanoparticles or core-shell nanoparticles from b) i) or b) ii), respectively, holding the resulting reaction mixture at a time ($t^4$) and temperature ($T^4$) (e.g., ($t^4$) 0.5 minutes to 24 hours at room temperature ($T^4$)) (whereby at least a portion of the PEG-silane conjugate molecules are adsorbed on at least a portion of the surface of the core nanoparticles or core-shell nanoparticles from b)), subsequently heating the resulting reaction mixture at a time ($t^5$) and temperature ($T^5$) (e.g., ($t^5$) 1 hour to 24 hours at 40° C. to 100° C. ($T^5$)), whereby nanoparticles surface functionalized with PEG groups comprising a ligand or core-shell nanoparticles surface functionalized with PEG groups comprising a ligand are formed, optionally, subsequently adding at room temperature to the resulting reaction mixture comprising nanoparticles surface functionalized with PEG groups comprising a ligand or core-shell nanoparticles surface functionalized with PEG groups comprising a ligand a PEG-silane conjugate (the concentration of PEG-silane no ligand is between 10 mM and 75 mM) (e.g., PEG-silane conjugate dissolved in a polar aprotic solvent such as, for example, DMSO or DMF), holding the resulting reaction mixture at a time ($t^6$) and temperature ($T^6$) (e.g., ($t^6$) 0.5 minutes to 24 hours at room temperature ($T^6$)) (whereby at least a portion of the PEG-silane conjugate molecules are adsorbed on at least a portion of the surface of the nanoparticles surface functionalized with PEG groups comprising a ligand or at least a portion of the core-shell nanoparticles surface functionalized with PEG groups comprising a ligand a PEG-silane conjugate), and heating the resulting mixture from at a time ($t^7$) and temperature ($T^7$) (e.g., ($t^7$) 1 hour to 24 hours at 40° C. to 100° C. ($T^7$)), whereby nanoparticles surface functionalized with PEG groups and PEG groups comprising a ligand or core-shell nanoparticles surface functionalized with PEG groups and polyethylene groups comprising a ligand are formed.

10. A method of any one of the preceding Statements, where at least a portion of or all of the PEG-silane has a reactive group on a terminus of the PEG moiety opposite the terminus conjugated to the silane moiety of the PEG-silane conjugate (is formed from a heterobifunctional PEG compound) and after formation of the nanoparticles surface functionalized with PEG groups having a reactive group, and, optionally, PEG groups, core-shell nanoparticles surface functionalized with PEG groups having a reactive group, and, optionally, PEG groups, are reacted with a second ligand (which can be the same or different than the ligand of the nanoparticles surface functionalized with PEG groups and PEG group comprising a ligand or the core-shell nanoparticles surface functionalized with PEG groups and polyethylene groups comprising a ligand) functionalized with a second reactive group (which can be the same or different than the reactive group of the nanoparticles surface functionalized with PEG groups and PEG group comprising a ligand or the core-shell nanoparticles surface functionalized with PEG groups and polyethylene groups comprising a ligand) thereby forming nanoparticles surface functionalized with polyethylene groups functionalized with a second ligand and, optionally, PEG groups, core-shell nanoparticles surface functionalized with polyethylene groups functionalized with a second ligand and PEG groups and, optionally, PEG groups.

11. A method of one of Statements 8 or 9, wherein at least a portion of or all of the PEG-silane has a reactive group on a terminus of the PEG moiety opposite the terminus conjugated to the silane moiety of the PEG-silane conjugate (is formed from a heterobifunctional PEG compound) and after formation of the nanoparticles surface functionalized with PEG groups and, optionally, having a reactive group, and, optionally, PEG groups, core-shell nanoparticles surface functionalized with PEG groups having a reactive group, and, optionally, PEG groups, are reacted with a second ligand (which can be the same or different than the ligand of the nanoparticles surface functionalized with PEG groups and PEG group comprising a ligand or the core-shell nanoparticles surface functionalized with PEG groups and polyethylene groups comprising a ligand) functionalized with a second reactive group (which can be the same or different than the reactive group of the nanoparticles surface functionalized with PEG groups and PEG group comprising a ligand or the core-shell nanoparticles surface functionalized with PEG groups and polyethylene groups comprising a ligand) thereby forming nanoparticles surface functionalized with polyethylene groups functionalized with a second ligand and, optionally, PEG groups, core-shell nanoparticles surface functionalized with polyethylene groups functionalized with a second ligand and PEG groups and, optionally, PEG groups.

wherein at least a portion of the PEG-silane has a reactive group on a terminus of the PEG moiety opposite the terminus conjugated to the silane moiety of the PEG-silane conjugate (is formed from a heterobifunctional PEG compound) and after formation of the nanoparticles surface functionalized with PEG groups having a reactive group, core-shell nanoparticles surface functionalized with PEG groups having a reactive group, nanoparticles surface functionalized with PEG groups having a reactive group and PEG groups comprising a ligand, or core-shell nanoparticles surface functionalized with PEG groups having a reactive group and polyethylene groups comprising a ligand the reactive group are reacted with a second ligand functionalized with a reactive group (which can be the same or different than the ligand of the nanoparticles surface functionalized with PEG groups and PEG group comprising a ligand, or core-shell nanoparticles surface functionalized with PEG groups and polyethylene groups comprising a ligand) thereby forming nanoparticles surface functionalized with PEG groups and polyethylene groups functionalized with a second ligand, core-shell nanoparticles surface functionalized with PEG groups and polyethylene groups functionalized with a second ligand, nanoparticles surface functionalized with PEG groups comprising a ligand, or core-shell nanoparticles surface functionalized with PEG groups and polyethylene groups comprising a ligand that is functionalized with the second ligand.
12. A method of any one of the preceding Statements, wherein the method further comprises one or more post-synthesis processes.
13. A composition comprising a plurality of core or core-shell nanoparticles surface functionalized with PEG groups or core-shell nanoparticles surface functionalized with PEG groups, wherein at least 90%, 95%, 96%, 97%, 98%, 99%, 99.5%, or 99.9% of the core nanoparticles have a size (e.g., longest dimension) of 2 to 15 nm or core-shell nanoparticles have a core size (e.g., longest dimension) of 2 to 15 nm and/or a size (e.g., longest dimension) of 2 to 50 nm and the composition has not been subjected to any particle-size discriminating (particle size selection/removal) processes (e.g., filtration, dialysis, or centrifugation).
14. A composition of Statement 13, where the core is a silica core or the core and shell of the core-shell nanoparticles is a silica shell.
15. A composition of Statement 13, where the core is an aluminosilicate core or the core of the core-shell nanoparticles is an aluminosilicate core and shell of the core-shell nanoparticles is a silica shell.
16. A composition of any one of Statements 13 to 15, where at least a portion or all of the polyethylene groups comprise one or more ligand.
17. A composition of any one of Statements 13 to 17, where the core nanoparticles surface functionalized with PEG groups or core-shell nanoparticles surface functionalized with PEG groups have one or more dye molecules (e.g., NIR dye molecules) encapsulated therein.
18. A composition of Statement 18, wherein the core is an aluminosilicate core.
19. A composition of any one of Statements 18 or 19, where the number of dye molecules per core is 1 to 7.
20. The composition of Statement 12, wherein the PEG chain length of ligand-PEG-silane is longer than the PEG chain length of PEG-silane thereby ensuring accessibility of the functional ligands (e.g., if a PEG-silane with 6-9 EO monomers is used, the PEG chain of the ligand-PEG-silane has at least 12 EO monomers or if a PEG-silane with 12 EO monomers is used, the PEG chain of the ligand-PEG-silane has at least 16 EO monomers).
21. The composition of Statement 12, further comprising radioisotopes attached to the ligand groups (e.g., tyrosine residue or chelator of the ligand-functionalized particles or to the silica matrix of the PEGylated particles without specific ligand functionalization), for photoinduced electron transfer imaging.
22. The composition of Statement 21, wherein the radioisotopes are selected to be therapeutic, (e.g., $^{225}$Ac or $^{177}$Lu), thereby forming nanoparticles with radiotherapeutic properties.
23. The composition of Statement 12, wherein the composition comprises a drug-linker conjugate covalently attached to the functional ligands on the nanoparticles for drug delivery, wherein the linker group is configured to be cleaved by enzyme or acid condition in tumor for drug release.
24. A method for imaging of a region within an individual comprising: (a) administering to the individual the composition of one of Statements 13-23 of the present disclosure, wherein the nanoparticles comprise one or more dye molecules; (b) directing excitation electromagnetic radiation (e.g., light) into the subject, thereby exciting at least one of the one or more dye molecules; (c) detecting excited electromagnetic radiation (e.g., light), the detected electromagnetic radiation having been emitted by said dye molecules in the individuals as a result of excitation by the excitation electromagnetic radiation; and (d) processing signals corresponding to the detected electromagnetic radiation to provide one or more images (e.g. a real-time video stream) of the region within the subject.

The following examples are presented to illustrate the present disclosure. They are not intended to limiting in any matter.

Example 1

The following in an example of synthesis and characterization of nanoparticles of the present disclosure.

Ultrasmall fluorescent silica nanoparticles (SNPs) and core-shell SNPs surface functionalized with polyethylene glycol (PEG), specific surface ligands, and overall SNP size in the regime below 10 nm are of rapidly increasing interest for clinical applications due to their favorable biodistribution and safety profiles. Here, an aqueous synthesis methodology for the preparation of narrowly size-dispersed SNPs and core-shell SNPs with size control below 1 nm (e.g., at the level of a single atomic layer) is presented. Different types of fluorophores, including near infrared (NIR) emitters, can be covalently encapsulated. Brightness can be enhanced via addition of extra silica shells. This methodology further enables synthesis of <10 nm sized fluorescent core and core-shell SNPs with previously unknown compositions. In particular addition of an aluminum sol-gel precursor leads to fluorescent aluminosilicate nanoparticles (ASNPs) and core-shell ASNPs. Encapsulation efficiency and brightness of highly negatively charged NIR fluorophores is enhanced relative to the corresponding SNPs without aluminum. Resulting particles show quantum yields of ~0.8 (e.g., starting to approach the theoretical brightness limit). All particles may be PEGylated providing steric stability. Finally, heterobifunctional PEGs can be employed to introduce ligands onto the PEGylated particle surface of fluorescent SNPs, core-shell SNPS, and their aluminum containing analogues, producing ligand functionalized<10 nm NIR fluorescent nanoprobes. In order to distinguish these water based synthesis derived materials from the earlier alcohol-based modified Stöber process derived fluorescent core-shell SNPs referred to as Cornell dots or C dots, the SNPs and ASNPs described here and synthesized in water will be referred to as Cornell prime dots or C' dots and AlC' dots. These organic-inorganic hybrid nanomaterials may find applications in nanomedicine, including cancer diagnostics and therapy (theranostics).

The results of synthesis studies of ultrasmall SNPs using water as the reaction medium are presented. Combining fast hydrolysis, slow condensation and efficient PEG-silane induced termination of particle growth, precise size control of ultrasmall, <10 nm diameter, SNPs in steps below 1 nm, with narrow particle size distributions is demonstrated. By co-condensing different silane-conjugated fluorophores into the silica matrix this synthesis process can be used to produce <10 nm diameter fluorescent SNPs with optical characteristics tuned from the visible into the NIR part of the optical spectrum. Additional silica shells can be added to the synthesis protocol while keeping the overall particle diameter below 10 nm. This core-shell architecture leads to improved fluorescence brightness as compared to the parent cores. The water based synthesis approach is quite versatile and enables previously unknown inorganic compositions of the particles, without loss of particle size control. To that end as an example silica and mixed compositions derived from the addition of aluminum alkoxides as sol-gel precursors are investigated. The resulting growth conditions of these mixed inorganic NPs allow for more efficient incorporation of highly negatively charged NIR emitting fluorophores as compared to the plain silica based particles. At the same time the resulting NPs show enhanced quantum efficiency of encapsulated dye as compared to particles synthesized without the aluminum alkoxide addition. These aluminum containing fluorescent SNPs will be referred to as AlC' dots. Fluorescent SNPs, core-shell SNPs, and their aluminum containing analogues are PEGylated to provide steric stability. Finally, heterobifunctional PEGs are employed to introduce ligands onto the PEGylated particle surface of fluorescent SNPs and core-shell SNPS, as well as their aluminum containing analogues, producing ligand functionalized<10 nm NIR fluorescent nanoprobes for preclinical and clinical use in diagnostic and therapeutic applications. This is demonstrated using $\alpha_v\beta_3$ integrin-targeting cyclo (arginine-glycine-aspartic acid-D-tyrosine-cysteine), c (RGDyC) peptides used in earlier studies to target melanoma tumor in animal models and a first human clinical trial Besides the ability to synthesize size controlled and highly fluorescent silica-based nanoprobes for biotechnological and clinical applications, comparison of water-based particle growth pathways with those of the conventional Stöber process may contribute to a better fundamental understanding of the exact formation mechanisms of SNPs and other silica-based nanomaterials.

Experimental Section 2.1. Materials. All chemicals are used as received. Dimethyl sulfoxide (DMSO), isopropanol, (3-mercaptopropyl) trimethoxysilane (MPTMS), (3-Aminopropyl)triethoxysilane (APTES), tetramethyl orthosilicate (TMOS), tetraethyl orthosilicate (TEOS), polyethylene glycol chains (PEG, molar mass around 400), aluminum-tri-sec-butoxide, 2.0 M ammonia in ethanol and 27 wt % ammonium hydroxide are purchased from Sigma Aldrich. Methoxy-terminated poly (ethylene glycol) chains (PEG-silane, molar mass around 500) are purchased from Gelest. Heterobifunctional PEGs with maleimide and NHS ester groups (mal-PEG-NHS, molar mass around 800) are purchased from Quanta BioDesign. Acetic acid is purchased from Mallinckrodt. Cy5 and Cy5.5 florescent dyes are purchased from GE. Rhodamine green (RhG) and tetramethylrhodamine (TMR) fluorescent dyes are purchased from Life Technologies. DY782 florescent dye is purchased from Dyomics and CW800 florescent dye is purchased from Li-cor. Absolute anhydrous 99.5% ethanol is purchased from Pharmco-Aaper. Cyclo (Arg-Gly-Asp-D-Tyr-Cys) peptide, c (RGDyC), is purchased from Peptide International. Deionized water (DI water) is generated using a Millipore Milli-Q system.

When reaction conditions are listed as occurring overnight, the time the reaction can occur can range from about 8 hours to about 24 hours or even greater.

2.2. Synthesis of sub-10 nm PEGylated silica nanoparticles. For the synthesis of 4.2 nm PEGylated silica nanoparticles (SNPs), 1 ml of 0.02M ammonia aqueous solution, which is prepared by mixing 100 µl of 2.0M ammonia in ethanol and 10 ml DI water, is added into 9 ml of DI water (resulting concentration of ammonia hydroxide 0.002M, see Table 1). The solution is stirred at room temperature for 10 minutes and 0.43 mmol of TMOS is then added under vigorous stirring (resulting concentration of TMOS 0.043M, see Table 1) and the solution is stirred at room temperature overnight (12-24 hours). Following that, 0.21 mmol of PEG-silane is added and the solution is stirred at room temperature overnight (12-24 hours). In the next step, the temperature is increased to 800° C. and stirring is stopped. The solution is then left static at 800° C. overnight. Afterwards, the solution is cooled to room temperature and then transferred into a dialysis membrane tube (Pierce, Molecular Weight Cut off 10.000). The solution in the dialysis tube is dialyzed in 2000 ml DI-water and the water is changed every day for six days to wash away any remaining reagents. The particles are then filtered through a 200 nm syringe filter (Fisher brand) to remove any aggregates or dust present in the particle solution. The resulting particle solution is then subjected to long term storage at room temperature and characterization including TEM, DLS, TGA and NMR. The molar ratios of the reaction are 1 TMOS: 0.093 ammonia: 0.49 PEG-silane: 1292 H$_2$O. Particles size was varied by tuning synthesis conditions. Details are summarized in Table 1.

TABLE 1

Synthesis condition of particles with different size.

| DLS Diameter | Temperature | Concentration of TMOS | Concentration of Ammonia hydroxide | Particle Growth Period |
|---|---|---|---|---|
| 2.4 nm | RT | 0.011M | 0.002M | 20 hrs |
| 3.1 nm | RT | 0.022M | 0.002M | 20 hrs |
| 3.7 nm | RT | 0.043M | 0.002M | 10 mins |
| 4.2 nm | RT | 0.043M | 0.002M | 20 hrs |
| 4.5 nm | RT | 0.043M | 0.02M | 20 hrs |
| 5.2 nm | RT | 0.043M | 0.06M | 20 hrs |
| 5.9 nm | 50 | 0.043M | 0.002M | 20 hrs |
| 6.5 nm | 65 | 0.043M | 0.002M | 20 hrs |
| 7.3 nm | 80 | 0.043M | 0.002M | 20 hrs |

Note that the same particles with the same size dispersity and structure control can also be synthesized using a 27 wt % ammonium hydroxide solution instead of the 2.0M ammonia in ethanol as the ammonium hydroxide source as long as the solution pH is tuned to around 8. This indicates that the key to this C' dot particle synthesis is the correct pH plus water environment for optimized silica reaction kinetics. Small contamination of ethanol (around 10 ul ethanol in a 10 ml reaction) does not have any detectable effect in the particle synthesis as it does not greatly disturb the reaction kinetics.

2.3. Synthesis of sub-10 nm PEGylated fluorescent silica nanoparticles. Cy5, Cy5.5, RhG, TMR, DY782 and CW800 dyes with maleimido functionality are first conjugated to MPTMS in DMSO with a molar ratio fluorophore: MPTMS=1:25. The silane-conjugated fluorophore is then added together with TMOS into the synthesis solution to co-condense into the particles. The molar ratio of silane-conjugated fluorophore to TMOS is around 1:1000. The remainder of the synthesis protocol is the same as described for the synthesis of the 4.2 nm particles under section 2.2.

In order to obtain the most precise fluorescence characterization of the fluorescent particles, any fluorophore-labeled particles prepared in this study are further purified by GPC after the filtration step to further remove any remaining free dye molecules, which could disturb FCS and emission spectra measurements, and to maximize the fluorescent particle product purity. In detail, the cleaned particle solution is concentrated by about 30 times using spin-filters (GE healthcare Vivaspin with MWCF 30 k) and then purified by GPC column (see section 2.8 for details). Since the solvent used in the GPC setup is a 0.9 wt % NaCl solution, the purified particles are finally transferred back to DI water using spin-filters for further characterizations and long-term storage. In order to transfer the particles back to DI water, the purified particles are first concentrated by 30 times using spin-filters (GE healthcare Vivaspin with MWCF 30 k). DI water is then added into the concentrated particle solution to dilute it back to the normal volume. This process is repeated for at least 8 times to decrease the concentration of NaCl to close to zero. The purified particle sample is then subjected to long-term storage at 40° C. and for further characterizations.

2.4. Synthesis of sub-10 nm PEGylated core-shell silica nanoparticles and sub-10 nm PEGylated fluorescent core-shell silica nanoparticles. The synthesis protocol for PEGylated core-shell SNPs is the same as that for the synthesis of the 4.2 nm particles except a shell addition step is added after the formation of the particles and before the addition of PEG-silane. One day after the addition of TMOS (and silane-conjugated fluorophore for the synthesis of PEGylated fluorescent core-shell SNPs) the reaction is cooled down to room temperature if a temperature above room temperature was applied for core particle formation (see Table 1).

The solution is then diluted 5 times with DI water. After that, a mixture of TEOS and DMSO (volume ratio 1:4) is dosed into the solution under vigorous stirring at room temperature. The volume of each dose is 10 ul and the time gap between doses is 30 minutes. 50 doses are added for the addition of one layer of silica shell resulting in a shell thickness close to 0.5 nm (particle size increase by around 1 nm). This process is repeated until the desired layers of shells (e.g., 1-4) are added. During the shell addition, the solution pH decreases as the result of the addition of extra TEOS and the formation of silicic acid. To keep the pH at neutral for optimized reaction kinetics, around 2 ml of 0.02M ammonium hydroxide solution is further added into the reaction solution after the deposition of every two layers of silica shell. Afterwards, 1.05 mmol of PEG-silane (same PEG-silane concentration as the PEGylation of core particles) is added and 800° C. heat treatment is applied following the same procedure as described for the 4.2 nm particle synthesis. Purification steps are applied as described above in section 2.3.

2.5. Synthesis of sub-10 nm PEGylated aluminosilicate nanoparticles and PEGylated aluminosilicate core-silica shell aluminosilicate nanoparticles. For the synthesis of sub-10 nm PEGylated aluminosilicate nanoparticles (ASNPs), 1 ml of 0.5N HCl solution is added into 9 ml of DI water and the solution is stirred for 10 minutes. Following that, 0.43 mmol of TMOS and 0.043 mmol of aluminum-tri-sec-butoxide (dissolved in isopropanol with volume ratio 1:9) are added under vigorous stirring at room temperature. 10-15 minutes later, 0.21 mmol PEG-silane is added followed by switching back of solution pH to neutral via adding about 140 μl of 27 wt % ammonium hydroxide. The final pH is double checked with pH paper. Afterward, the solution is kept at 800° C. overnight without stirring. The remainder of the synthesis protocol follows the same procedures as described for the synthesis of 4.2 nm particles in section 2.2.

For the synthesis of core-shell ASNPs, 0.21 mmol PEG (molecular mass around 400) is added instead of PEG-silane before the reaction pH is switched back to neutral. After the reaction pH is switched back to neutral, a mixture of TEOS and DMSO (volume ratio 1:8) is dosed into the solution under vigorous stirring at room temperature. The volume of each dose is 10 μl and the time gap between doses is 30 minutes. 50 doses are added for the addition of one layer of silica shell resulting in a shell thickness close to 0.5 nm (particle size increase by around 1 nm). This process is repeated until the desired layers of shells (e.g., 2) are added. Afterwards, 0.21 mmol PEG-silane is added and the 800° C. heat treatment is applied without stirring. The remainder of the synthesis protocol follows the same procedures as described for the synthesis of 4.2 nm particles in section 2.2. The addition of PEG-silane before switching solution pH back to neutral is not necessary, but this can improve the monodispersity of synthesized ASNPs and prevent their aggregation during the process of changing pH.

2.6. Synthesis of sub-10 nm PEGylated fluorescent aluminosilicate nanoparticles and sub-10 nm PEGylated fluorescent aluminosilicate core-silica shell aluminosilicate nanoparticles covalently encapsulating Cy5 or Cy5.5 fluorophores. In order to covalently encapsulate fluorophores into ASNPs, silane-conjugated Cy5 or Cy5.5 fluorophore is added right after the addition of TMOS and aluminum-tri-sec-butoxide using the same conjugation conditions and dye concentration as described in section 2.3. The remainder of the synthesis protocol is the same as described for the synthesis of blank ASNPs in section 2.5 and purification steps are applied as described above in section 2.3.

2.7. PEGylated particle surface modification with easily accessible ligands. In order to functionalize the surface of any of the PEGylated particles in this study with, for example, c (RGDyC) peptide ligands, the heterobifunctional NHS-PEG-mal is first conjugated with APTES in DMSO to produce mal-PEG-silane. The concentration of NHS-PEG-mal in DMSO is around 0.22M. The reaction mixture is left at room temperature under nitrogen overnight. As the next step c (RGDyC) is then added into the DMSO solution and the solution is left at room temperature under nitrogen overnight. The molar ratio of c (RGDyC):NHS-PEG-mal: APTES is 1.1:1.0:0.9 to ensure every heterobifunctional PEG condensed on the particle surface has c (RGDyC) attached. Afterwards, the produced c (RGDyC)-PEG-silane is added followed by the addition of PEG-silane in the PEGylation step during nanoparticle synthesis. Different molar ratios of c (RGDyC)-PEG-silane: PEG-silane can be used to vary the amount of ligands on the particle surface. For example, a molar ratio of c (RGDyC)-PEG-silane:PEG-silane of about 1:40 gives around 22 c (RGDyC) ligands per 7 nm diameter particle, while decreasing the ratio to 1:400 will result in about 5 c (RGDyC) ligands per 7 nm particle. The remainder of the synthesis is the same as that described for the conventional PEGylation in section 2. The same methodology can be applied to all particles described in this study for producing surface functionalized probes, including blank and fluorescent SNPs, core-shell SNPS, and their aluminum containing analogues, all with different types of covalently encapsulated fluorophores. Other ligands that can be used in this way include, but are not limited to, other linear and cyclic peptides, antibody fragments, various DNA and RNA segments (e.g. siRNA), therapeutic molecules including drugs and radioisotopes and their respective chelating moieties, as well as combinations thereof.

2.8. Gel permeation chromatography characterization (GPC). GPC characterization is performed using a BioLogic LP system equipped with a 275 nm UV detector and with resin Superdex 200 from GE healthcare. While the blank SNPs can hardly be detected by the 275 nm UV detector due to the low absorbance of silica, the fluorescent SNPs show strong signals in the GPC setup because the encapsulated fluorophores have absorbance overlapping with the 275 nm detecting channel. As a result, GPC can be used to further increase the purity of cleaned C' dot products for characterization and further clinical applications. Before usage, the GPC system is calibrated by protein standards from Bio-Rad, which are a mixture of thyroglobulin, bovine y-globulin, chicken ovalbumin, equine myoglobin, and vitamin B12 with known molar masses. Afterwards, around 400 μl of particle solution is injected into the GPC setup and fractions are collected by a BioFrac fraction collector. A detailed analysis of different GPC factions is displayed in FIG. 15. By collecting the particle factions, the particle product purity can be further maximized.

2.9. Characterization of particle morphology. Transmission electron microscopy (TEM) images are taken using a FEI Tecnai T12 Spirit microscope operated at an acceleration voltage of 120 kV. Hydrodynamic particle sizes and size distributions are measured by dynamic light scattering (DLS) using a Malvern Zetasizer Nano-SZ operated at 200° C. Each DLS sample is measured three times and results are superimposed in the respective figures in this paper. Number percentage curves are used to present the measurement results. The average diameter of each sample is calculated by averaging the mean diameters of number percentage curves from three measurements.

2.10. Characterization of fluorophore encapsulating particles. Absorbance spectra of samples are measured by a Varian Cary 5000 spectrophotometer. By varying sample concentration, the absorbance spectra of different samples are matched and thus the optical density of different samples are adjusted to be the same. Afterwards, the absorbance-matched samples are subjected to emission scans using a Photon Technologies International Quantamaster spectrofluorometer. The peak intensity of emission spectra of particles is divided by the peak intensity of the absorption-matched solution of free dye for quantum efficiency enhancement calculations.

Fluorescent auto-correlation spectroscopy (FCS) measurements are conducted using an FCS setup. A 488 nm solid-state laser is used as the laser source for RhG fluorophore. A 543 nm HeNe laser is used as the laser source for TMR fluorophore. A 633 nm solid-state laser is used as the laser source for Cy5 and Cy5.5 fluorophores. A 785 nm solid-state laser is used as the laser source for DY782 and CW800 fluorophores. The hydrodynamic size, brightness per particle and particle concentration are obtained from fits of the FCS auto-correlation curves. Dividing particle concentration obtained from FCS by fluorophore concentration obtained from absorbance measurements, the number of fluorophores per particle is calculated as described.

2.11. 29Si and 27Al solid state NMR characterization. The 29Si cross-polarization (CP)/magic angle spinning (MAS) NMR experiments are carried out on a Bruker Advance NMR spectrometer with a 9.4 T magnet using a probe head for rotors of 4 mm diameter. During the 29Si CP/MAS NMR experiments the samples are spun at 7.00 kHz rotation frequency at the magic angle. For the final spectra, up to 3200 scans are accumulated using CP with ramped proton powers during the 5 ms CP contact times and detection with TPPM proton decoupling. The 29Si CP/MAS NMR scans are accumulated with repetition time of 3 s due to the probe duty cycle.

The 27Al NMR experiments are performed on a Bruker Avance NMR spectrometer with a 16.45 T magnet (182.47 MHz 27Al Larmor frequency) using a probe head for rotors of 2.5 mm diameter. Potassium alum serves as external 27Al NMR chemical shift secondary reference (at −0.033 ppm) and for calibration of the 90 degree pulse lengths and rf power. The final 27Al NMR MAS spectra are acquired with a nominally 10 degree direct excitation pulse at 95 kHz rf field strength, adding up to 6144 scans with 100 ms repetition times, while spinning the sample at 15.00 kHz at the magic angle. The 27Al background of the probe head and rotor are characterized by acquiring the spectrum of an empty rotor under identical conditions and subtracting it from the sample spectra.

2.12. Thermogravimetric analysis (TGA). The particle solution is first frozen in liquid nitrogen and then left under vacuum at −200° C. over three nights to dry. The powder after freeze-drying is further left under vacuum at 600° C. overnight. The dried out particle sample is then subjected to TGA. The TGA is conducted using a TA Instruments Q500 thermogravimetric analyzer. During the measurement, the temperature is increased from room temperature to 1000° C. with a ramp of 100° C./min and then remains at 1000° C. for 2 h to fully exclude any residual water. Afterward, the temperature is further increased to 6000° C. with a ramp of 100° C./min removing any organic moieties and leaving pure inorganic silica or aluminosilicate behind. The average amount of PEG chains on a particle is then estimated according to these TGA results.

2.13. Molecular model of c (RGDyC) functionalized C' dot. Based on the full analysis of the C' dot structure, e.g. core size, shell thickness, PEG surface density, number of surface ligands, and number of fluorophores encapsulated, a schematic molecular model was generated displaying the architecture of a C' dot at the atomic level with realistic scale. In order to do this, we first constructed a 4 nm $SiO_2$ sphere which is a continuous random network of Si and O atoms. The coordinates of each Si and O atoms inside the network are generated by reverse Monte Carlo simulation of a silica glass. A total of about 800 $SiO_2$ units present inside the core particle are used, which agrees well with a calculation using the density of amorphous silica. Following this, a volume inside this core particle is manually created where one encapsulated Cy5 fluorophore is drawn. Afterwards, around 100 PEG chains and 16 c (RGDyC)-functionalized PEG chains covalently bonded to the silica particle surface are added manually. The final drawing represents one C' dot particle with a ~3 nm core, ~0.5 nm shell, one encapsulated Cy5 fluorophore, around 100 PEG chains, and 16 c (RGDyC) ligands on surface. It is important to note that the model is not the result of a true simulation, but is rather a scaled schematic drawing which provides a realistic visualization of the relative size scale of the different building blocks of one C' dot particle.

Results and Discussion 3.1. Controlled Blank Silica Nanoparticle Growth. FIG. 1 presents the aqueous particle synthesis pathways pursued in this study together with the chemical and physical structures of the products. As detailed herein, <10 nm diameter SNPs are synthesized in pure water, typically at room temperature, with tetramethyl orthosilicate (TMOS) as silica source and ammonium hydroxide as base catalyst. Upon the formation of particles, PEG-silane with molar mass around 500 g/mole is added into the reaction vessel to terminate particle growth. A subsequent heat treatment at elevated temperature (80° C.) is then applied to enhance the condensation degree of PEG-silane on the particle surface. The synthesized particles are cleaned though dialysis to remove reaction reagents and then filtered by a 200 nm syringe filter to remove any aggregates or dust before further characterizations. The particle growth period is defined by the time window between the addition of TMOS and the addition of PEG-silane. As particle PEGylation is a part of the synthesis, the particles are already surface modified with PEG chains once synthesized and are stable (e.g. in high salt containing buffer solutions). Particle size is controlled by varying reaction parameters including concentration of TMOS, concentration of ammonium hydroxide, length of particle growth period, and reaction temperature.

Figure 2:
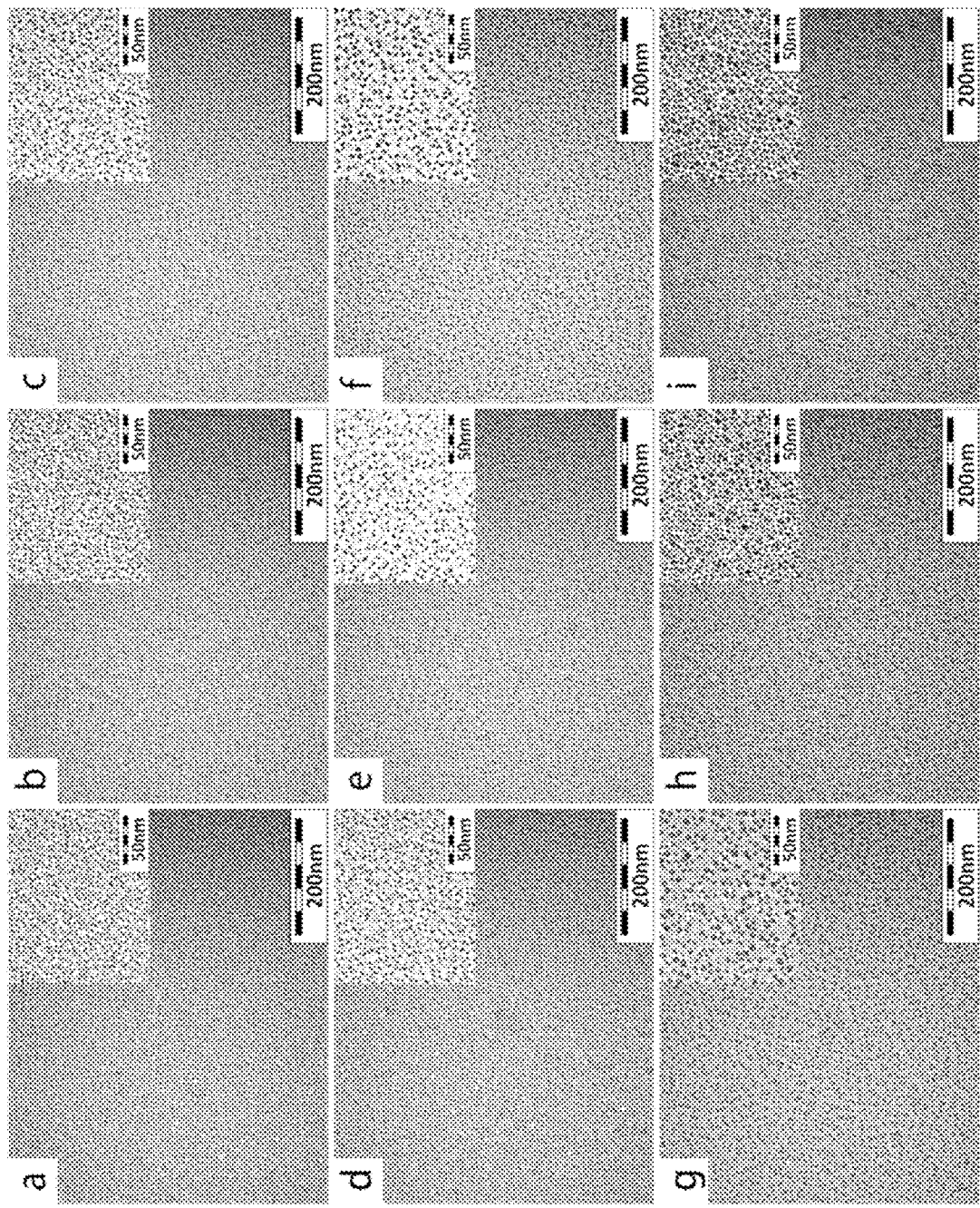
FIG. 2 shows characterization of blank SNPs (i.e. without fluorophore encapsulation) (a-j). (a-i) show TEM images at two different magnifications (insets) of blank SNPs with the following average diameters as measured by DLS in aqueous solution: (a) 2.4 nm, (b) 3.1 nm, (c) 3.7 nm, (d) 4.2 nm, (e) 4.5 nm, 5.2 nm, (g) 5.9 nm, (h) 6.5 nm and (i) 7.3 nm. (j) Size distributions of blank SNPs with varying average diameters as measured by DLS in aqueous solution. (k-n) Characterization of Cy5-encapsulated fluorescent SNPs (C' dots) with different average diameters: 4.3 nm, 4.7 nm, 5.2 nm, 5.9 nm, 6.2 nm, 6.8 nm, 7.3 nm and 7.8 nm. The average diameters are measured by FCS. (k) shows FCS autocorrelation curves; (l) shows absorbance (matched) and emission spectra; (m) shows FCS derived number of fluorophores per particle; (n) shows FCS measured (columns) and calculated (dots) fluorescence brightness per particle of fluorescent SNPs with varying average diameters as compared to free dye in aqueous solution.
Figure 2:
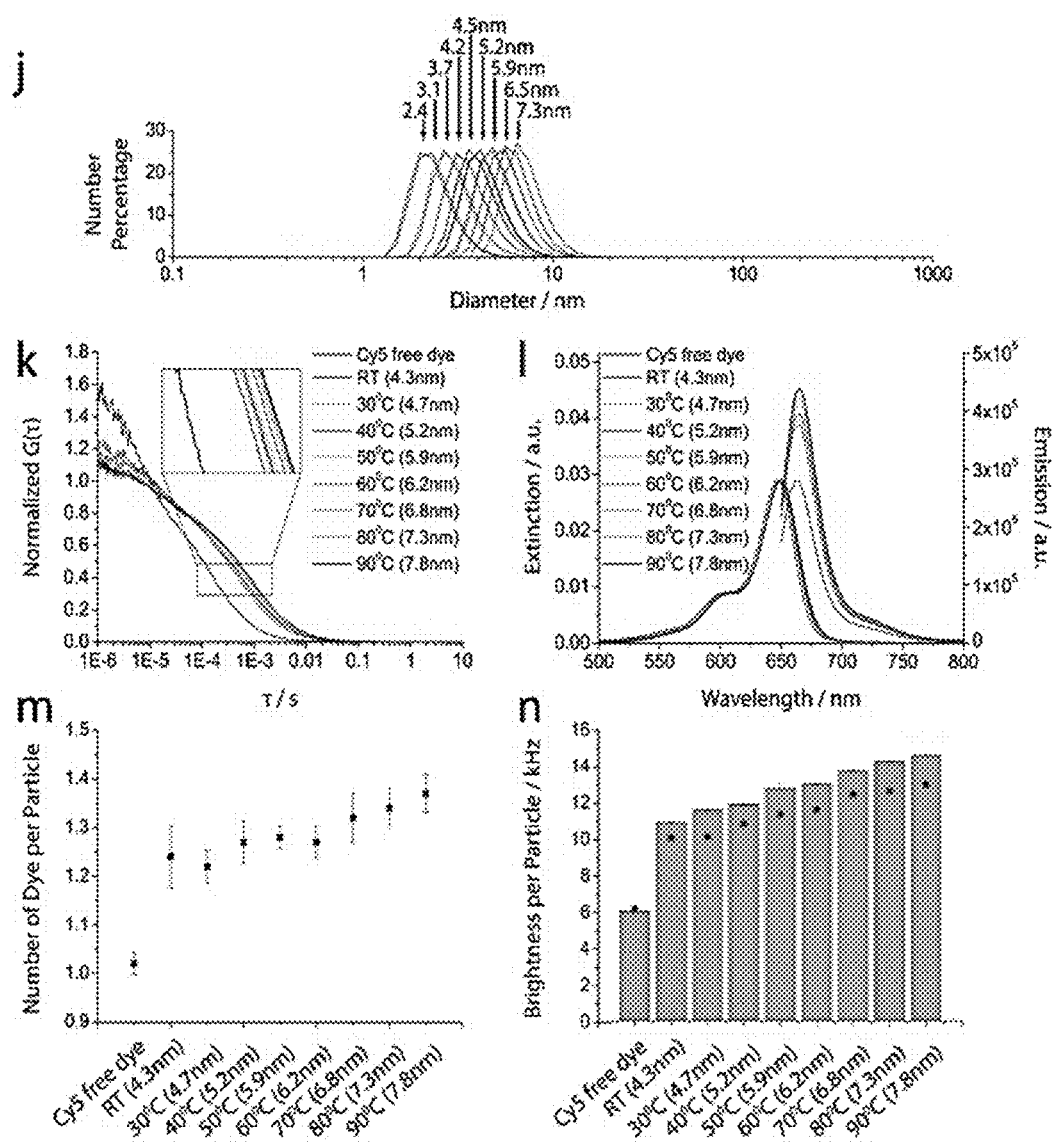
Figure 8:
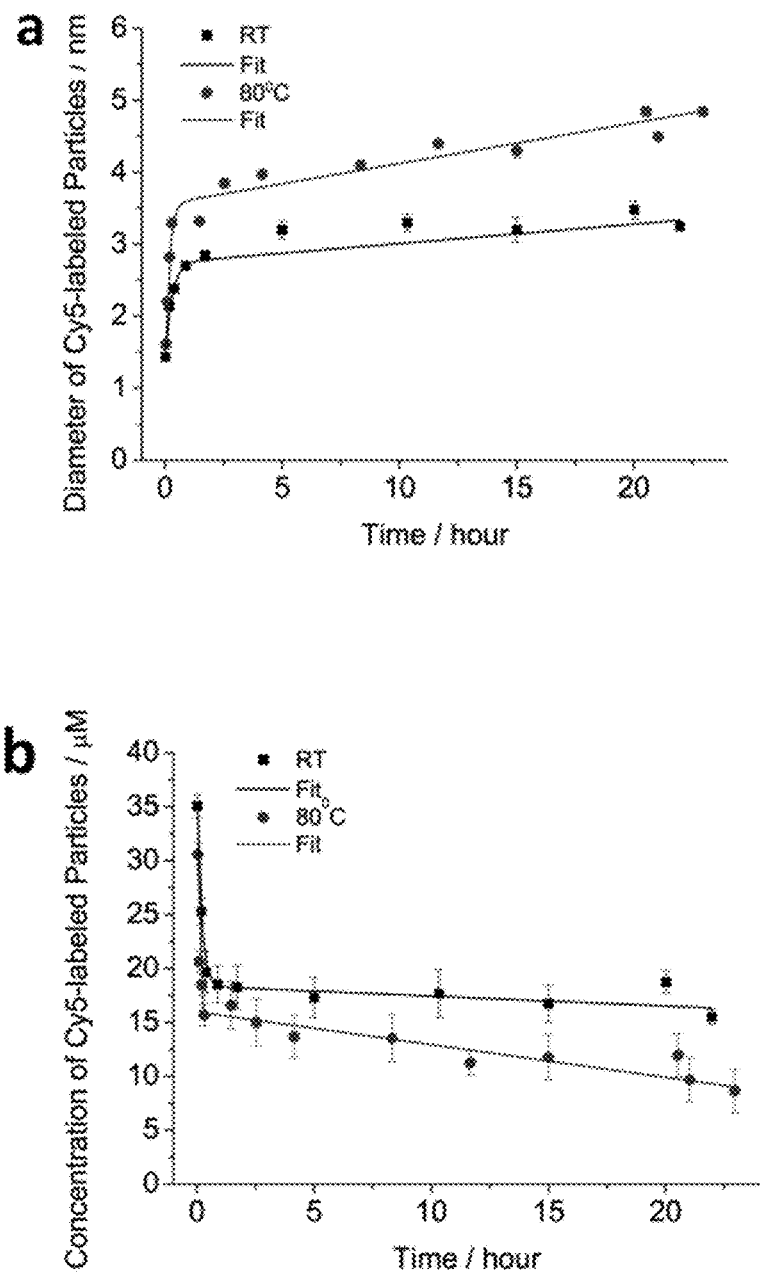
FIG. 8 shows in-situ FCS measurement results. (a) particle diameter and (b) particle concentration during the reaction and particle growth.
Figure 9:
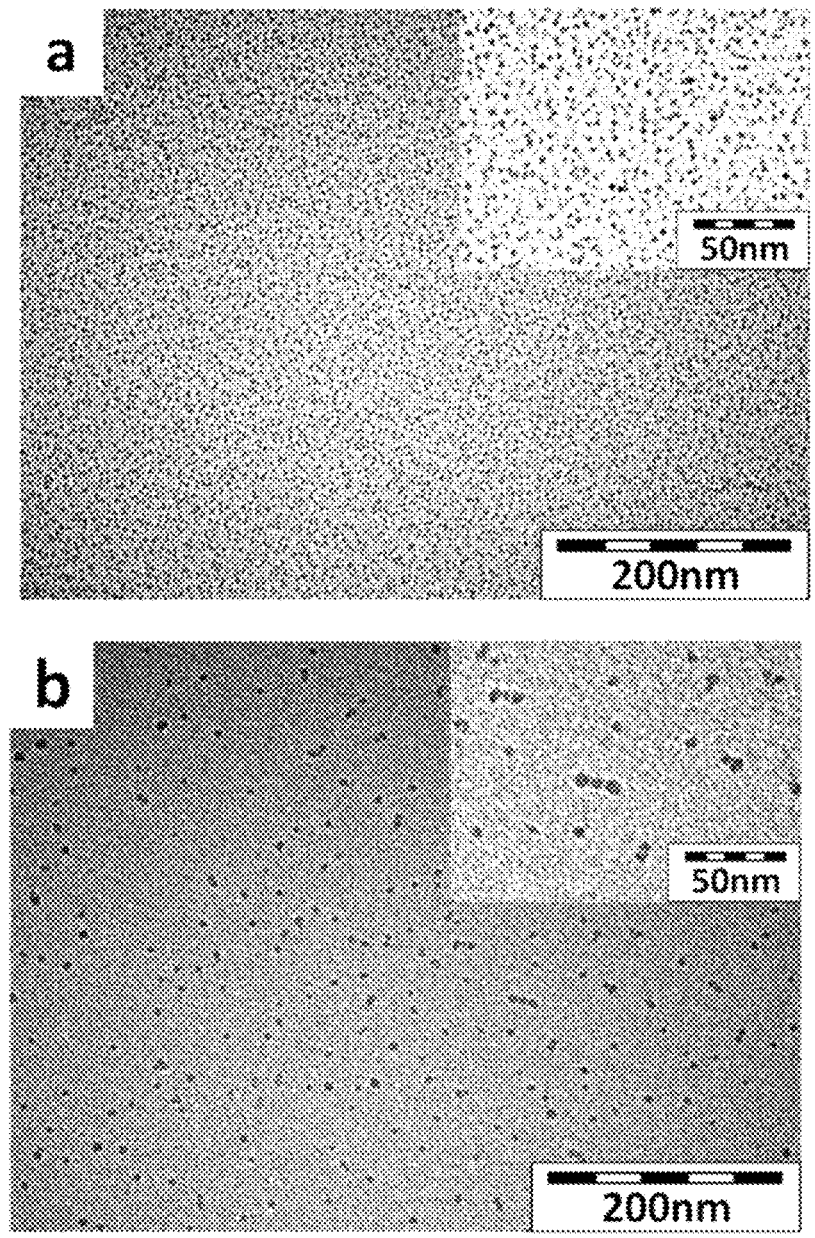
FIG. 9 shows TEM images of (a) particles synthesized at room temperature and (b) particles first synthesized at room temperature and then subjected to 80° C. heat treatment for another three days before growth is terminated by PEG-silane addition.

FIG. 2a-i display transmission electron microscopy (TEM) images at two different magnifications of particles grown under different conditions, revealing the size and size distribution control. For example, FIG. 2d shows 4.2 nm diameter SNPs synthesized using the following parameters: room temperature, 0.043M TMOS, 0.002M ammonium hydroxide, and 12-24 hours growth period. The diameter of 4.2 nm is determined by dynamic light scattering (DLS), while the particle diameter as obtained from TEM image analysis is only around 2-3 nm. The particle size measured by DLS is slightly larger than that by TEM because DLS measures hydrodynamic size which includes PEG chains and hydration layers, while TEM only provides information about the diameter of the projected silica core. Shortening the particle growth period from 24 hours to 10 minutes, the synthesized particle diameter decreases from 4.2 nm to 3.7 nm (FIG. 2c). Further decrease of the growth period does not result in the decrease of particle size, but to a loss of control of over size distribution. This suggests that the particles go through a rapid growth period during the first 10 minutes due to high precursor concentration, followed by a slow growth mode due to controlled aggregation (see FIGS. 8 and 9) of existing silica clusters. To further decrease particle size, the growth period of particles is left at 20 hours, but the concentration of silica source, TMOS, is decreased from 0.043M to 0.011M. As a result, the synthesized particle diameter decreases from 4.2 nm to 2.4 nm (FIGS. 2a and 2b). This is because the decrease of TMOS concentration leads to a lower hydrolyzed silica precursor concentration, which in turn leads to slower particle growth. Applying the 4.2 nm particle synthesis parameters, except increasing the concentration of ammonium hydroxide from 0.002M to 0.06M (thereby changing pH from ~8 to about ~10), the average particle diameter increases from 4.2 nm to 5.2 nm (FIGS. 2e and 2f). An increase in pH generally causes an increase of hydrolysis rate and decrease of condensation rate. Since the hydrolysis of TMOS in water is always fast, most likely the decrease of condensation rate is the dominant effect, leading to the lower particle concentration and bigger particle size. In order to further increase particle size, the reaction temperature of the particle growth period is varied. Applying the 4.2 nm particle synthesis parameters, but increasing reaction temperature from room temperature to 80° C., the average particle diameter further increases from 4.2 nm to 7.3 nm (FIGS. 2g to 2i). This could be the result of two effects (see also FIG. 8), though other mechanisms are possible. First, due to a high surface energy of small particles, at higher temperature silicic acid rapidly condenses into bigger silica clusters with lower concentrations until the silicic acid as precursor is exhausted. Afterwards, since smaller particles are less stable at higher temperature, particles further slowly aggregate into bigger ones and particle size further increases.

To monitor particle formation during reaction, silane-conjugated Cy5 fluorophore is added together with TMOS to co-condense into silica particles. As a result, via tracing the fluorescence signal from Cy5 fluorophores using FCS, in-situ particle diameter and particle concentration could be monitored. As shown in FIGS. 8a and 8b, upon the addition of silica source(s), TMOS and silane-conjugated Cy5 fluorophores hydrolyze and condense into particles resulting in particle size increases and fluorophore concentration decreases. For both room temperature and 800° C. syntheses, particles go through a rapid growth period within the first 10 minutes due to the high concentration of silicic acid present in the reaction mixture. Afterwards, as silicic acid concentration is now depleted due to the initial particle nucleation and growth burst, particles grow slower through further controlled aggregation. Both the particle diameter and concentration results could be fitted by the following equation:

$$y = y_0 + Ae^{(-t/t_R)} + Bt$$

The exponential part represents the rapid particle formation kinetics at the beginning of the reaction and the linear part represents the kinetics of the subsequent controlled aggregation step. In the particle diameter equation, y is the average particle diameter at time t, A is the relative amplitude of particle growth from the fast particle formation kinetics with characteristic time $t_R$, B is the particle growth rate of the later controlled aggregation process and $y_0 + A$ is the initial size of silica precursor. Since the FCS traces the Cy5-silane whose hydrodynamic size is about 1.2-1.5 nm, the fitted values of $y_0 + A$ are consistent with the expectation. (Table 2) In the particle concentration equation, y is the precursor concentration (Cy5-labed silica cluster) at time t, A is the relative amplitude of particle growth contribution from the fast particle formation kinetics with characteristic time $t_R$, B is the decreasing rate of particle concentration in the later controlled aggregation process and $y_0 + A$ is the initial concentration of Cy5-silane. The fitted parameters are shown in the following table.

TABLE 2

| Synthesis condition of particles with different size | | | | | |
|---|---|---|---|---|---|
| | | $y_0$ | A | $t_R$ | B |
| Diameter | RT | 2.74 ± 0.07 nm | −1.30 ± 0.11 nm | 0.29 ± 0.05 hr | 0.03 ± 0.01 nm/hr |
| | 80° C. | 3.56 ± 0.11 nm | −2.39 ± 0.16 nm | 0.17 ± 0.03 hr | 0.06 ± 0.01 nm/hr |
| Concentration | RT | 18.36 ± 1.17 µM | 18.36 ± 1.70 µM | 0.18 ± 0.04 hr | −0.09 ± 0.06 µM/hr |
| | 80° C. | 15.97 ± 0.64 µM | 23.76 ± 2.35 µM | 0.06 ± 0.01 hr | −0.30 ± 0.05 µM/hr |

Compared to the room temperature synthesis, particles forming at 80° C. have bigger size and lower concentration at around 10 minutes right after the rapid growth period. This could be due to the fact that the particle surface energy is higher at higher temperature. This is also consistent with the finding that the fitted values of $t_R$ in both diameter and concentration equations are smaller at higher temperature, which indicates the higher rate. After 10 minutes, particle size continuously increases and particle concentration slightly decreases at 80° C. while at room temperature both changes are smaller. This suggests that at higher temperature particles tend more to aggregate into bigger ones through controlled aggregation due to the increase of surface energy. From the fitted value B, one can estimate the aggregation rate at different temperatures; it is around 0.03 nm/hr at room temperature and 0.06 nm/hr at 80° C.

In order to further demonstrate that particles grow through controlled aggregation at high temperature, a room temperature synthesis reaction is split into two parts 16 hours after the addition of TMOS and dye-silane at which moment the core particles have formed. One of the two particle batches is terminated by PEG-silane addition following the common synthesis procedure and the TEM image of the final product is shown in FIG. 9a. The other batch is subjected to 80° C. heat treatment for another 3 days, followed by reaction termination via addition of PEG-silane. As shown in FIG. 9b, the particles after high temperature treatment have a bigger size than the particles without high temperature treatment (FIG. 9a). Considering that most of the silica source has already condensed onto particles during the first day of reaction, this further particle growth at higher temperature is most likely the result of further growth via aggregation of smaller silica particles. This controlled aggregation could be caused by the fact that at high temperature the surface energy of small particles is so high that they tend to aggregate into bigger ones thereby lowing the overall free energy.

A comparison of size and size distributions as measured by DLS of the nine particle batches with different average diameters is displayed in FIG. 2j. The data demonstrates precise particle size control with steps below 1 nm. Considering that a single $SiO_2$ atomic layer is roughly around 0.4 nm thick, this is equivalent to controlling the particle growth at the level of the deposition of single atomic layers around the particles. Since this control is achieved by varying a combination of four reaction parameters, the synthesis system is endowed with a high degree of chemical versatility. This implies that narrowly size-dispersed ultrasmall SNPs can be synthesized under very different conditions, which should be compatible with other particle modification chemistries.

Compared to the conventional Stöber method, a difference of this process is that the reaction solvent is switched from alcohol to water, leading to the better-defined reaction kinetics for ultrasmall SNP growth. In water the hydrolysis rate of tetraalkoxysilanes, and particularly of TMOS, is greatly increased relative to alcohol, and thus even at close-to-neutral pH hydrolysis is still fast enough to generate a homogeneous silicic acid precursor solution.

Following the fast hydrolysis, water and near neutral pH further lead to fast condensation generating homogeneously sized SNP seeds at high concentrations. Keeping everything else constant, increasing/decreasing the concentration of TMOS leads to bigger/smaller particles through more/less monomer addition to the seeds. Since after seed formation no further monomer is provided by hydrolysis, the concentration of remaining silicic acid in solution is low and no significant amounts of silicic acid monomers can condense onto the existing seed particles, resulting in the production of small particles. As temperature increases, small particles can further aggregate into bigger ones due to decreased surface energy for bigger particles. Finally, terminating particle growth by PEG-silane addition adds another synthesis parameter by which particle size can be precisely controlled and final particle stability is greatly enhanced.

3.2. Controlled Fluorescent Silica Nanoparticle Growth. In experiments fluorescent dyes are covalently encapsulated for the production of fluorescent PEGylated SNPs. To this end, applying the 4.2 nm particle synthesis conditions, additional silane-conjugated Cy5 fluorophore is added into the reaction to co condense with TMOS into the silica matrix. Considering that the Cy5 fluorophore can be quenched by solutions at high base concentration, size control of the Cy5 doped particles is achieved by simply varying temperature, rather than ammonium hydroxide concentration. Synthesized particles are finally purified though gel permeation chromatography (GPC) after the regular cleaning steps to maximize particle purity and fully remove any residual free fluorophores which could otherwise falsify optical particle characterization results. The size of fluorescent particles from eight batches for which the reaction temperature was raised from room temperature to 90° C. is characterized by fluorescence correlation spectroscopy (FCS) (FIG. 2k). Compared to DLS, FCS shares a similar measurement mechanism, which extracts particle diffusion information from the autocorrelation of signal intensity fluctuations. However, instead of scattered light FCS uses fluorescence and thus is more sensitive to small particles or molecules whose scattering is weak.

Figure 10:
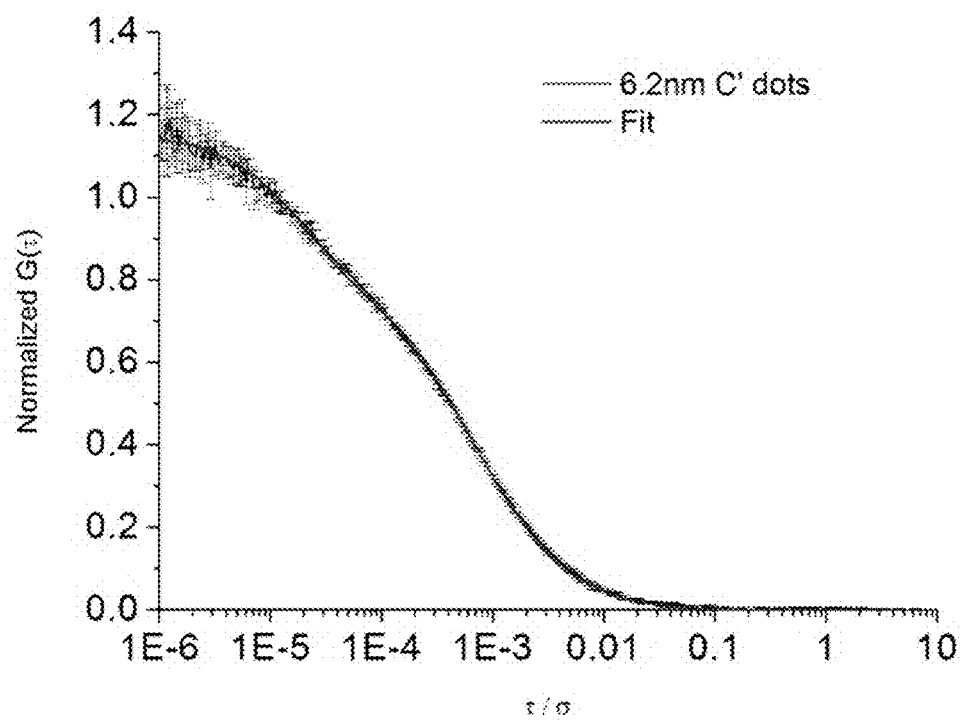
FIG. 10 shows 6.2 nm C' dot FCS characterization result as an example of a fit of a FCS autocorrelation curve.

FCS autocorrelation curves are fitted by the following equation:

$$G(\tau)=1+1/N \cdot 1/(1-A) \cdot (1-A+A \cdot e^{\wedge}(-\tau/\tau_R)) \cdot 1/(1+\tau/\tau_m)*1/\sqrt{(1+S^{\wedge}2 \cdot \tau/\tau_D)},$$

where S is the structure factor (ratio between the shorter axis and the longer axis of the elliptical focal spot of FCS setup), N is the average number of particles present in the focal spot, A is the amplitude of triplet state correction, $T_R$ is the characteristic time of triplet state and $\tau_D$ is the diffusion time. The structure factor S is obtained from the setup calibration and is fixed in the fit, while the values of N, A, $\tau_R$ and $\tau_D$ are obtained from the fit. FIG. 10 shows an example of this type of curve fitting. Based on the fitted parameters, average hydrodynamic diameter of particles, fluorescent brightness per particle and concentration of fluorescent particles can be obtained.

Figure 11:
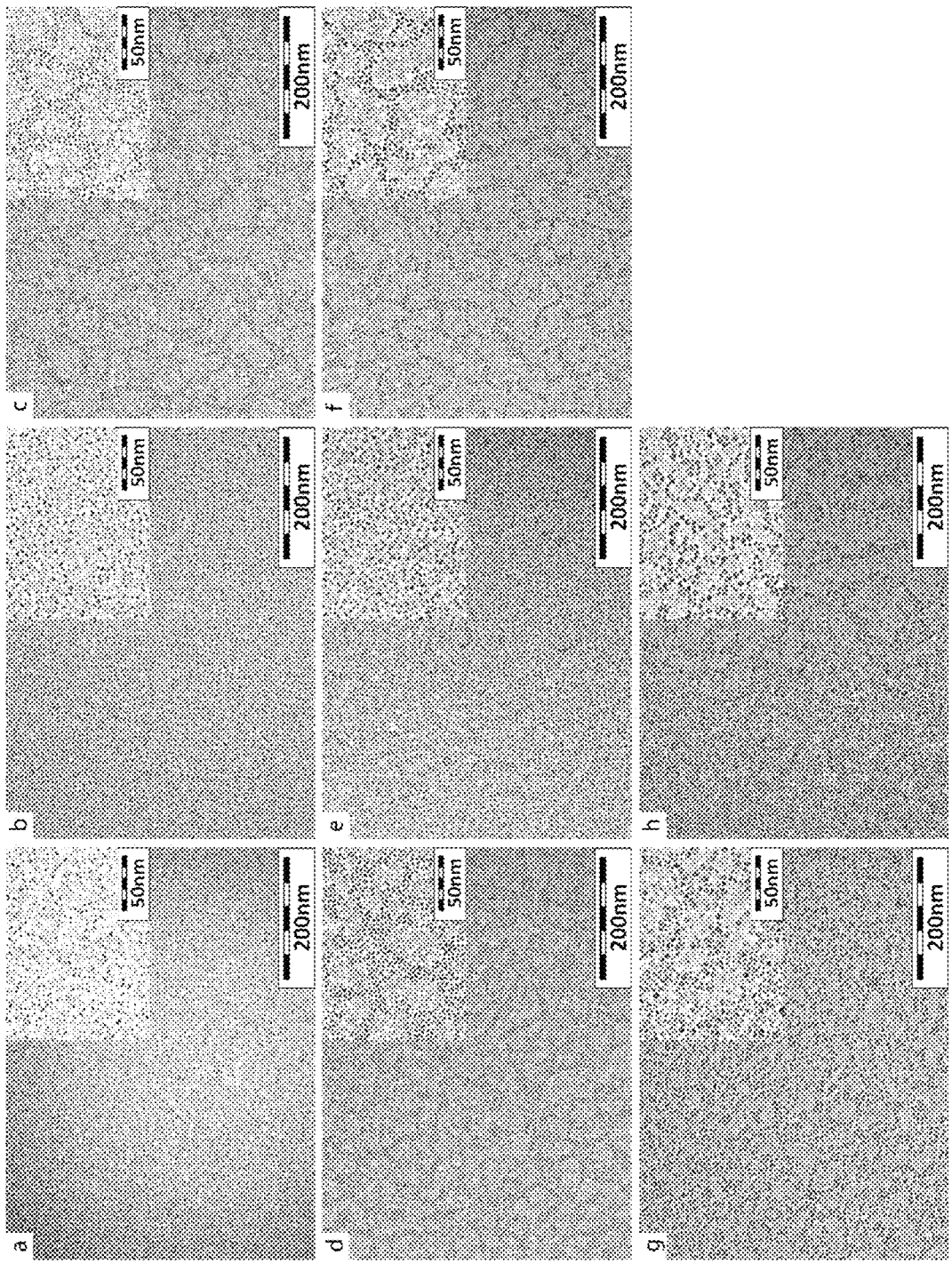
FIG. 11 shows TEM images of Cy5-encapsulated fluorescent and PEGylated SNPs (Cy5-C' dots, no shell) with varied average diameters as measured by FCS. (a) 4.3 nm, (b) 4.7 nm, (c) 5.2 nm, (d) 5.9 nm, (e) 6.2 nm, (f) 6.8 nm, (g) 7.3 nm, (h) 7.8 nm.

In FIG. 2k the shifts to the right of FCS autocorrelation curves, in particular moving from free dye to dye-encapsulating SNPs, indicate the slower diffusion times of the bigger particles. The average particle diameters are obtained via curve fitting (see FIG. 10 for an example) and vary from 4.3 nm to 7.8 nm in steps below 1 nm, covering a similar size range and single atomic layer size control as compared to the blank SNPs measured by DLS in FIG. 2j. Images of the fluorescent particles as obtained by TEM are shown in FIG. 11. Absorbance and emission spectra in water of these differently sized dots as compared to the free dye are shown in FIG. 2l. Absorbance matching all solutions reveals that silica encapsulated Cy5 dye is brighter than free dye, and that encapsulated Cy5 dye brightness increases with particle size. This brightness enhancement has been correlated to an increase in quantum yield due to a change in dielectric constant moving from water to silica, as well as the increased rigidity of the dye in the silica environment. As overall particle size increases, Cy5 fluorophores have a higher probability of being well encapsulated by the silica matrix leading to the observed higher quantum enhancement. The number of fluorophores per particle as well as the brightness per particle can be obtained from FCS derived solution concentration in conjunction with absorbance data. The results are displayed in FIGS. 2m and 2n, respectively. As suggested by FIG. 2n, each synthesized particle of the different synthesis batches contains around one to two fluorophores, and the number of fluorophores per particle slightly increases as particle size increases. Considering that one Cy5 fluorophore is around 1.2 nm in hydrodynamic diameter and has one negative charge (see molecular structure in FIG. 1) repelling it from the negatively charged silica, an average of 1-2 fluorophores per particle is a reasonable number. As shown in FIG. 2m, the brightness per particle as measured by FCS directly (from number of photons hitting the avalanche detector per dye/particle) is at least two times higher than the brightness per single Cy5 fluorophore in water, and increases as particle size increases. The brightness per particle can also be estimated from the product of the brightness per fluorophore and the number of fluorophores per particle (see black dots in FIG. 2m). While the overall trends in behavior are the same, it is interesting to note that the brightness per particle as measured directly by FCS consistently overestimates this calculated brightness value for all samples. This is in difference to particles synthesized via the Stöber method, in which FCS results underestimated the brightness. This difference in behavior may be due to improved particle cleaning procedures from free dye via GPC columns used in this study or due to different types of encapsulated fluorophores, though other mechanisms are possible. Overall the deviations in FIG. 2n are small, however, and trends for brightness per particles from FCS and calculations are consistent.

Figure 12:
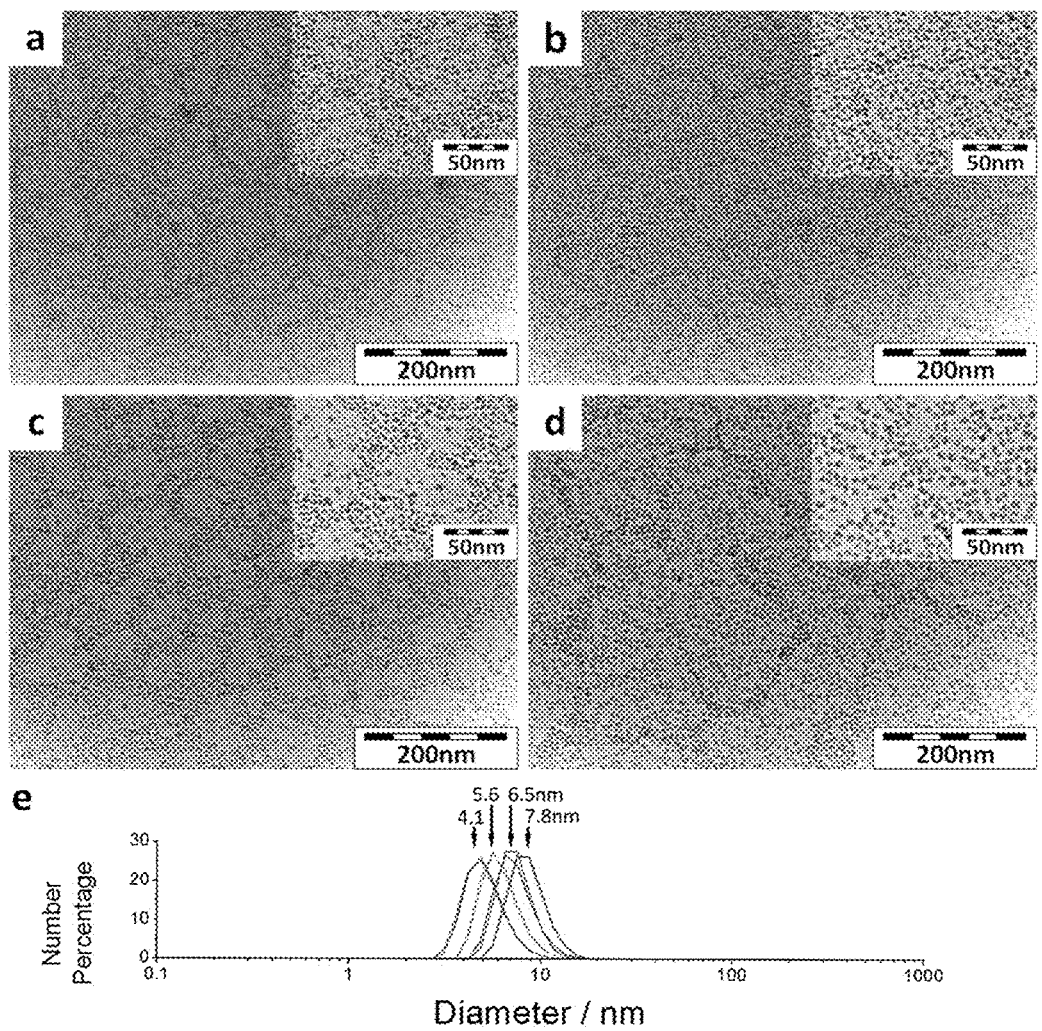
FIG. 12 shows TEM images of blank PEGylated core-shell SNPs (without fluorophores) with 0-3 layers of shells (a-d). (a) no shell (core/seed) 4.1 nm, (b) 1 shell, 5.6 nm, (c) two shells, 6.5 nm, and (d) three shells, 7.8 nm. The average diameters are measured by DLS. (e) Diameter distribution of SNPs with 0-3 layers of shells as measured by DLS.

3.3. Controlled Fluorescent Core-Shell Silica Nanoparticle Growth. Additional silica shells are added to particles before PEGylation by further dosing extra silica source into the reaction (FIG. 1). Compared to the particle size control via varying temperature, in which particle growth follows the controlled aggregation pathway, particle growth by silica shell additions follows the monomer addition pathway. The concentration of hydrolyzed precursor, silicic acid, always stays below the critical concentration for secondary particle nucleation. This can be achieved by optimizing the amount of silica source dosed at any given time and the time gap between doses. However, simply dosing TMOS always results in even smaller average sizes of the final particles independent of dose and gap width employed. This suggests that the additional silica source forms secondary particles rather than condensing onto the surface of existing ones. This is because both hydrolysis and condensation of TMOS in water are fast; upon the addition of a single dose, as mixing via simple stirring may not be fast enough, secondary particle formation is difficult to suppress. In order to circumvent secondary particle nucleation, the silica source used in the shell additions is switched from TMOS to TEOS, because of its slower hydrolysis rate. By optimizing pH and dilution, the hydrolysis of TEOS can be tuned to be just a little bit slower than the time needed for a single does to thoroughly mix with the entire solution. In this way, once TEOS of each dose spreads out, it hydrolyzes and condenses onto the existing particles fairly fast. As a result, additional silica shells can be efficiently added without secondary particle nucleation, resulting in an increase of average particle size. This is first successfully demonstrated using the pure SNPs (without dye addition), starting from a core size of around 4 nm, and adding three successive shells leading to particle sizes of 5.6 nm (one shell), 6.5 nm (two shells), and 7.8 nm (three shells), see FIG. 12 for TEM and DLS data.

Figure 3:
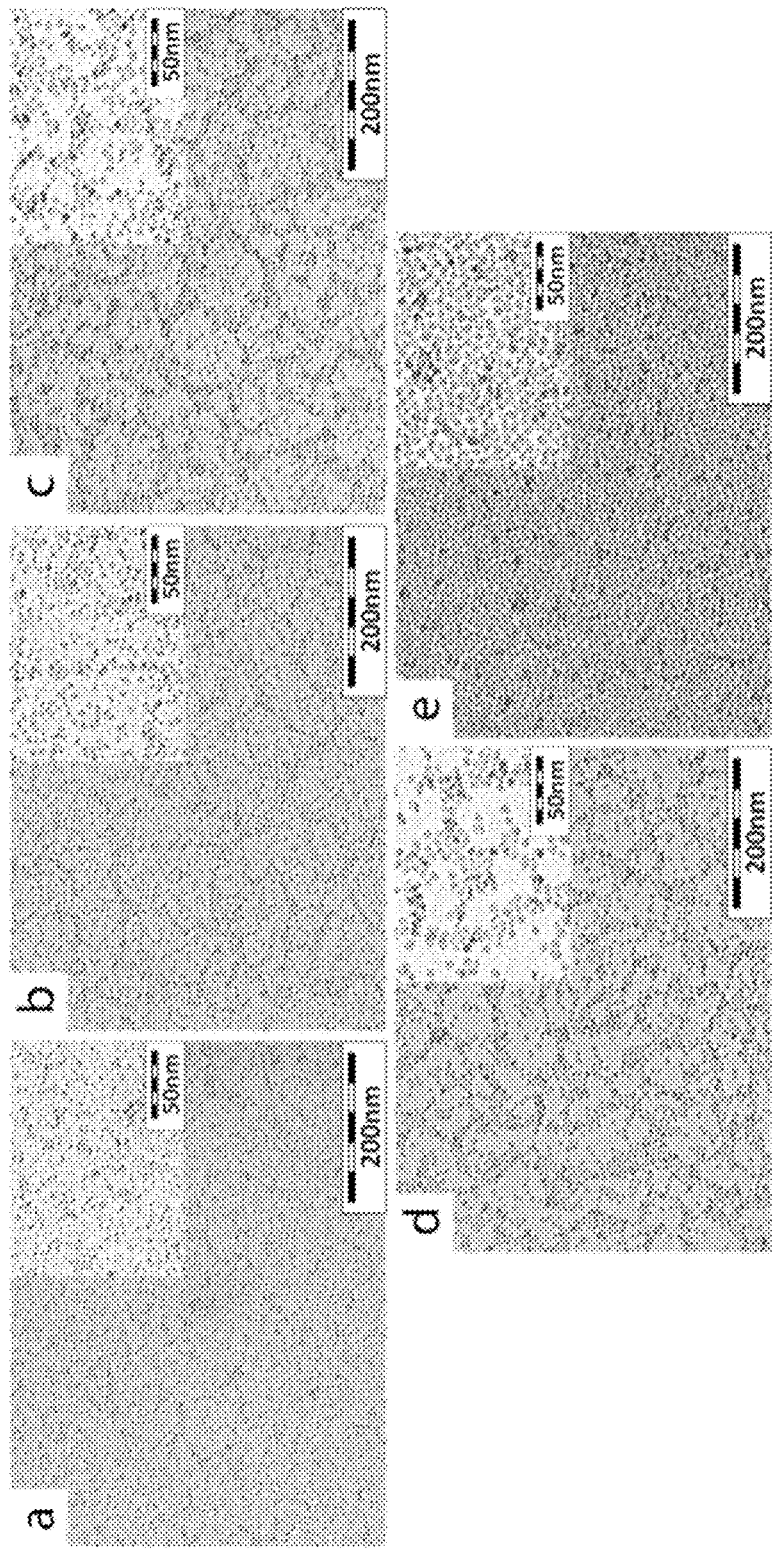
FIG. 3 shows TEM images at two different magnifications (insets) of Cy5-encapsulated fluorescent core-shell SNPs (C' dots) with 0 (core/seed) to 4 shells, and the following average diameters as measured by FCS: 5.0 nm (core/seed), 6.1 nm, 6.8 nm 7.8 nm and 8.7 nm (a-e). (f) Absorbance (matched) and emission spectra; (g) FCS autocorrelation curves; (h) FCS derived number of fluorophores per particle; (i) FCS measured (columns) and calculated (black dots) fluorescence brightness per particle of C' dots with 0 (core/seed) to 4 shells as compared to free dye in aqueous solution (see text).
Figure 3:
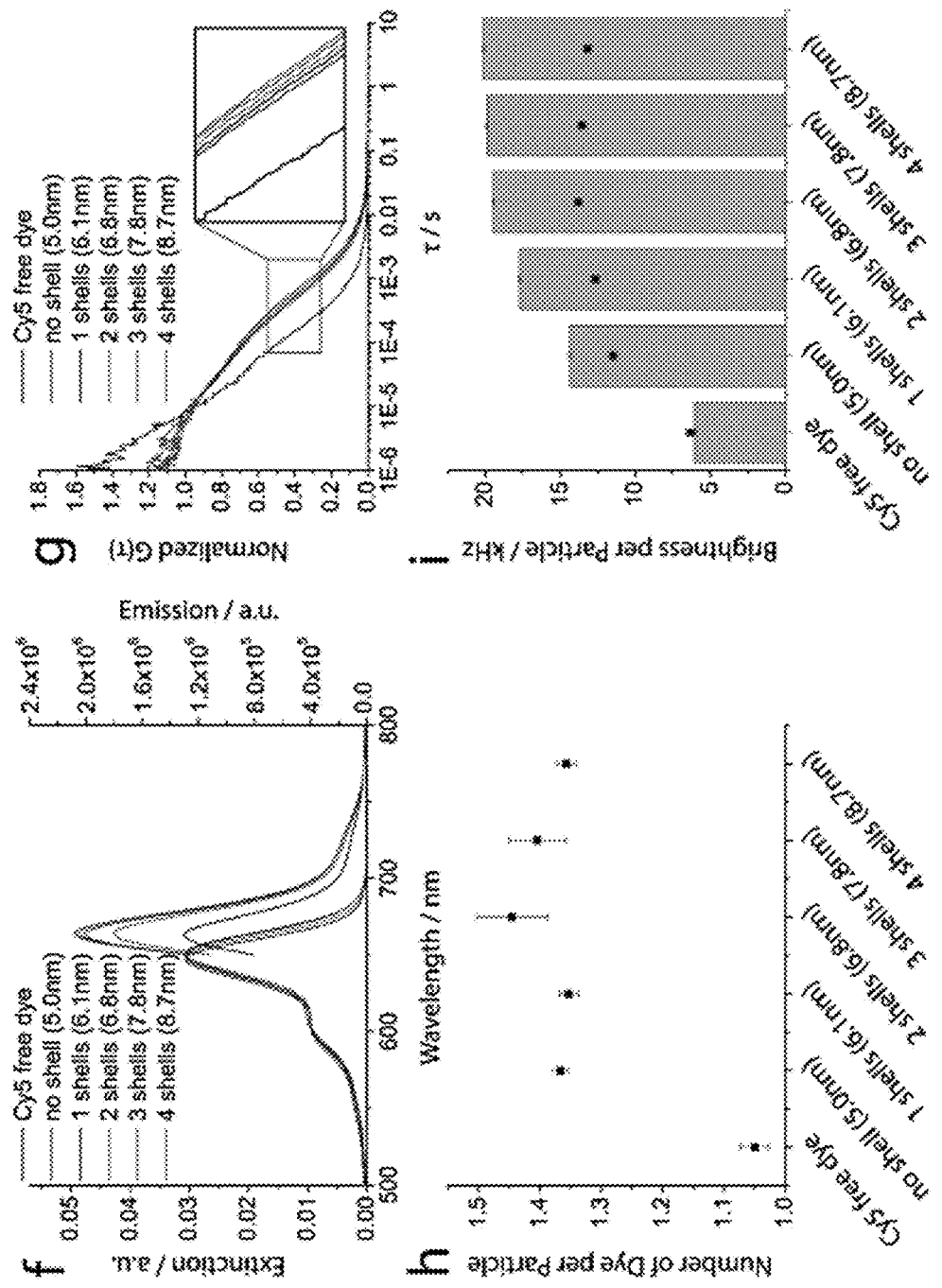

Subsequently, experiments are performed with Cy5 dye containing cores (FIG. 3). By adding 1 to 4 silica shells of about 1 nm thickness each to a 5 nm sized Cy5 doped particle core (seed), as revealed by FCS (FIG. 3g), Cy5 labeled fluorescent core-shell SNPs are synthesized. The TEM images of these particles, together with the parent core particle, are shown in FIG. 3a-e, revealing improved size control again at the single atomic layer level. Absorbance matched spectra as well as the corresponding emission spectra of these particles are compared to free dye in FIG. 3f. Results suggest a quantum enhancement over free Cy5 dye which increases from ~1.3 for the core particle to ~1.7 as the number of silica shells increases from 0 to 4. Similar to the case of increasing particle size without extra shells, this brightness increase most likely results from tighter silica encapsulation of Cy5 fluorophore with increasing shell number and a concomitant increase in rigidity through the local silica environment. As the number of shells increases, the FCS derived number of fluorophores per particle does not exhibit any obvious trend (FIG. 3h), which is different compared to the behavior of particles grown to different sizes in FIG. 2m. This further corroborates that in the shell addition experiments particles grow through monomer addition rather than controlled aggregation. Although the number of fluorophores per particle remains the same, as a result the enhancement of per dye brightness contributes to an increase of particle brightness as observed by FCS (see FIG. 3i).

Figure 13:
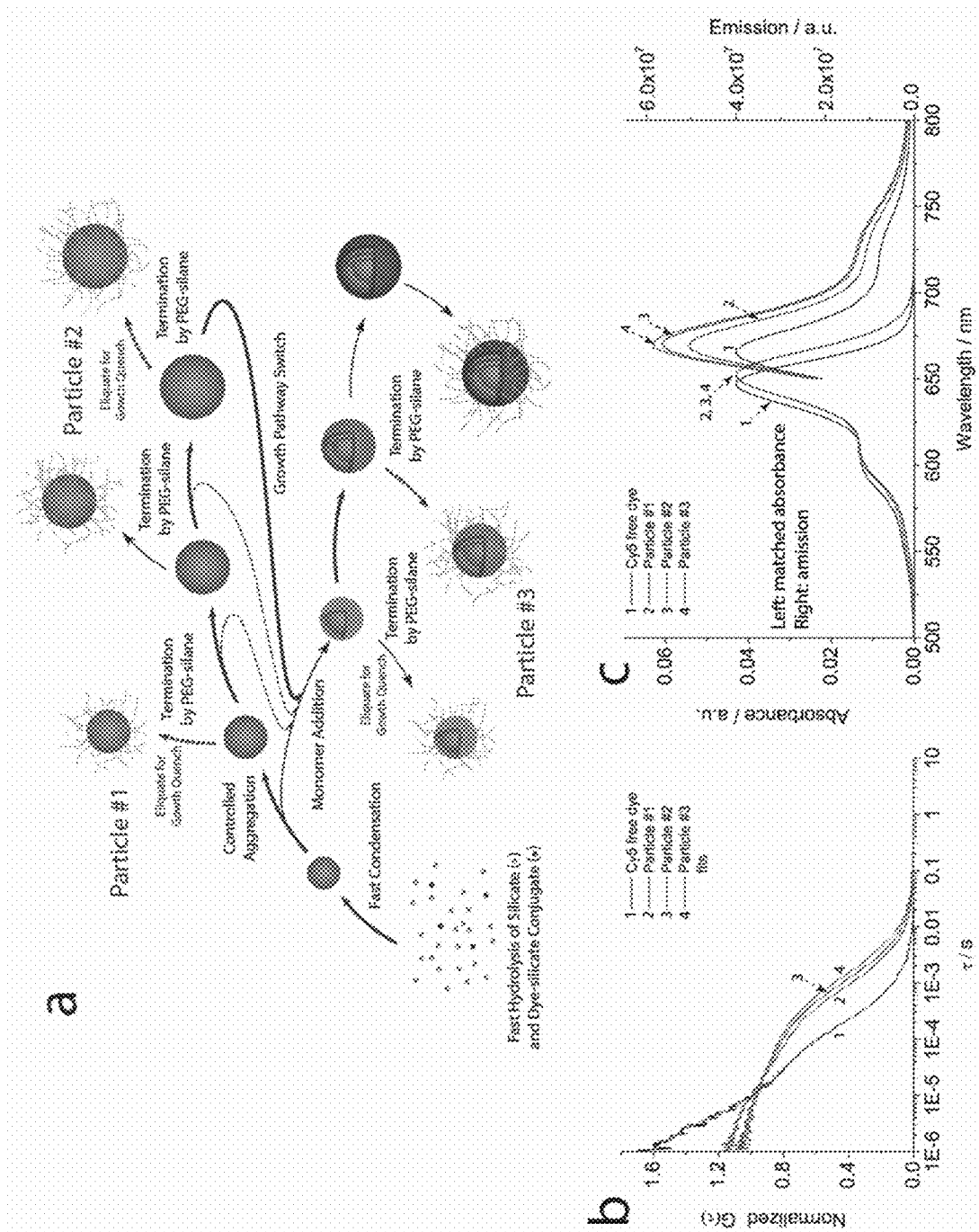
FIG. 13 shows switching the particle growth mechanism in a single synthesis. As highlighted by the path in (a), the growth of the forming particles first goes through controlled aggregation followed by monomer addition. Three sets of particles are produced from this synthesis through quenching the particle growth at different reaction time points via addition of PEG-silane. The resulting particles are characterized by (b) FCS and (c) optical absorbance/emission measurements.

With the water-based synthesis process described here, the size of SNP cores can be tuned via controlled aggregation while extra silica shells can be added via monomer addition (FIG. 1). In order to show the principle that these two particle growth pathways can be switched in a single synthesis of fluorescent core-shell SNPs, a batch of particles is grown first through controlled aggregation by varying reaction temperature, then through monomer addition by further dosing extra silica source. Small amounts of particles are aliquoted for PEGylation at different synthesis moments and then characterized. Results show a consistent increase of particle size as well as of encapsulated dye quantum enhancement during the synthesis (for details see FIG. 13). Results demonstrate that the architecture of <10 nm fluorescent core-shell SNPs, via core diameter and shell thickness, can be tuned at the sub nanometer single atomic layer level by the particle growth conditions described herein.

In order to prove the principle that these two particle growth pathways (e.g. controlled aggregation and monomer addition) can be switched in a single synthesis, a batch of particles is processed first through controlled aggregation by varying reaction temperature, then through monomer addition by further dosing extra silica source. Small amounts of sample solution are aliquoted at different synthesis points in order to quench particle growth via PEGylation. Refer to the path of FIG. 13a as the synthesis pathway. By characterizing the growing particles quenched at different time points, details of the particle growth process could be revealed. Here, the synthesis conditions for ~5 nm particles is first applied (room temperature). 24 hours after the addition of TMOS, ⅓ of the reaction solution is aliquoted and PEGylated to generate particle #1 (FIG. 13a). The remaining ⅔ of the reaction solution is then heated to 80° C. and maintained at this temperature for 48 hours followed by cooling down to room temperature. Afterwards, half of the remaining reaction solution is aliquoted and PEGylated to generate particle #2. The remaining half of the reaction solution is further subjected to deposition of two extra layers of silica shell. Particles are then PEGylated to generate particle #3. As shown in Table 3, while the diameter of particle #1 is 5.9 nm, the diameter of particle #2 increases to 9 nm after heat treatment. This increase of particle size is due to the controlled aggregation of small particles at high temperature. This aggregation also increases the number of dyes per particle from 1.4 to 2.6. After dosing extra silica source into the reaction solution, a thin silica shell is added onto the existing particle surface through monomer addition and the particle diameter further increases to 11.4 nm. As a result, particle #3 has an estimated core size slightly smaller than 9 nm and a silica shell with thickness around 1 nm. Since it has the same core size as particle #2, the number of dyes per particles remains about the same. However, the quantum enhancement of encapsulated dyes slightly increases from 1.7 to 1.8 due to the fact that the extra silica source further densifies the core matrix and the silica shells further protects the dyes inside the core. As a result, the number of dyes per particle could be increased by expanding the core size while the quantum efficiency could be enhanced by adding a thin layer of blank silica shell. The brightness of a <10 nm particle could be optimized by precisely tuning both the core size and shell thickness through selecting the desired particle growth pathway.

TABLE 3

Characterization results of three sets of particles quenched at different synthesis time points. Diameter and brightness are derived from FCS measurements while the # of dyes per particle is calculated from steady-state absorbance measurements and FCS concentration results.

|  | FCS Diameter | # of Dyes per Particle | Relative Quantum Enhancement | Relative brightness compared to free dye |
|---|---|---|---|---|
| Cy5 | 1.3 nm | 1.2 | 1 | 1 |
| Cy5 | 1.3 nm | 1.2 | 1 | 1 |
| Particle #1 | 5.9 nm | 1.4 | 1.3 | 2.2 times |
| Particle #2 | 9.0 nm | 2.6 | 1.6 | 3.3 times |

Figure 4:
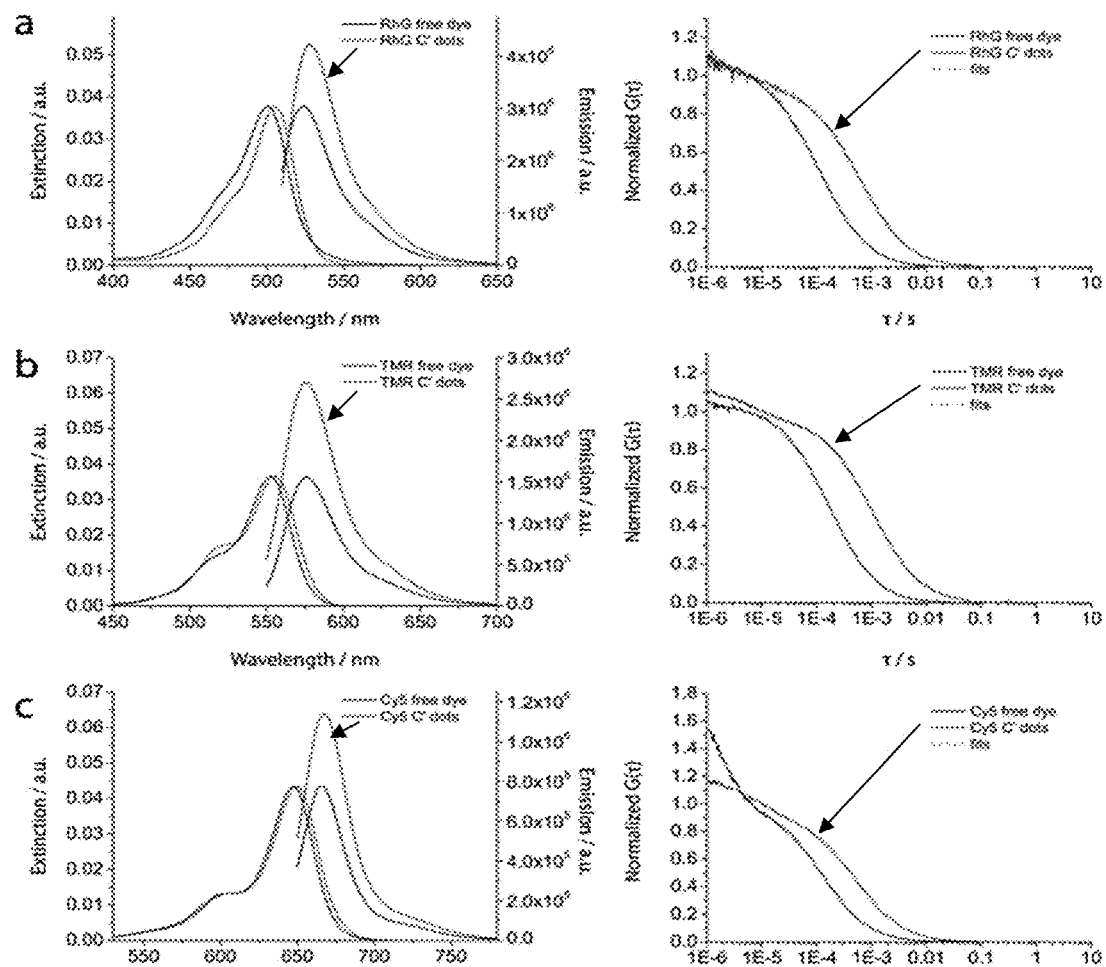
FIG. 4 shows absorbance (matched) and emission spectra (left) as well as FCS characterization (right) of C' dots derived from different types of fluorophores (a-f). (a) RhG, (b) TMR, (c) Cy5, (d) Cy5.5, (e) DY782 and (f) CW800. (g) Normalized absorbance and emission spectra of C' dots with different dyes/colors. (h) A photo showing the solution appearance of C' dots derived from different color dyes. From left to right: RhG, TMR, Cy5, Cy5.5, DY782 and CW800.
Figure 4:
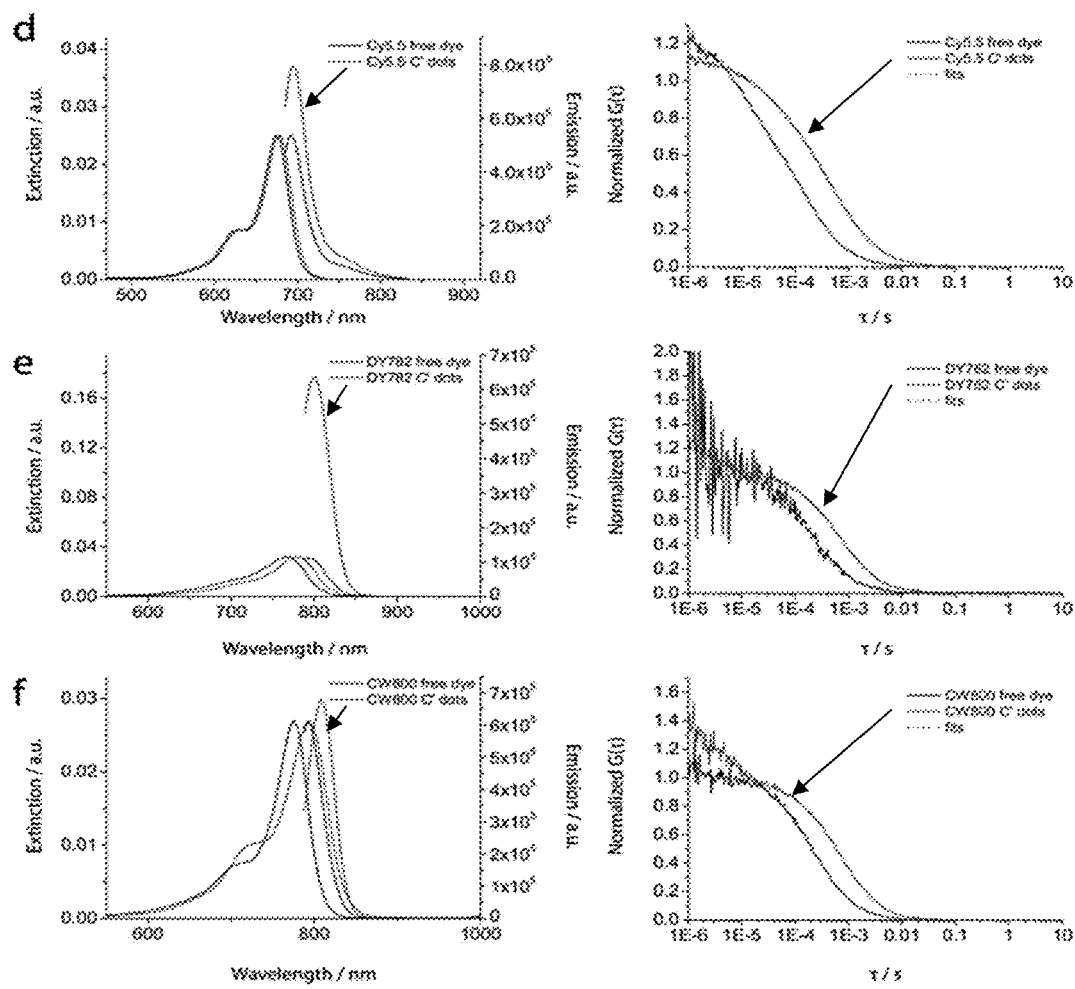
Figure 4:
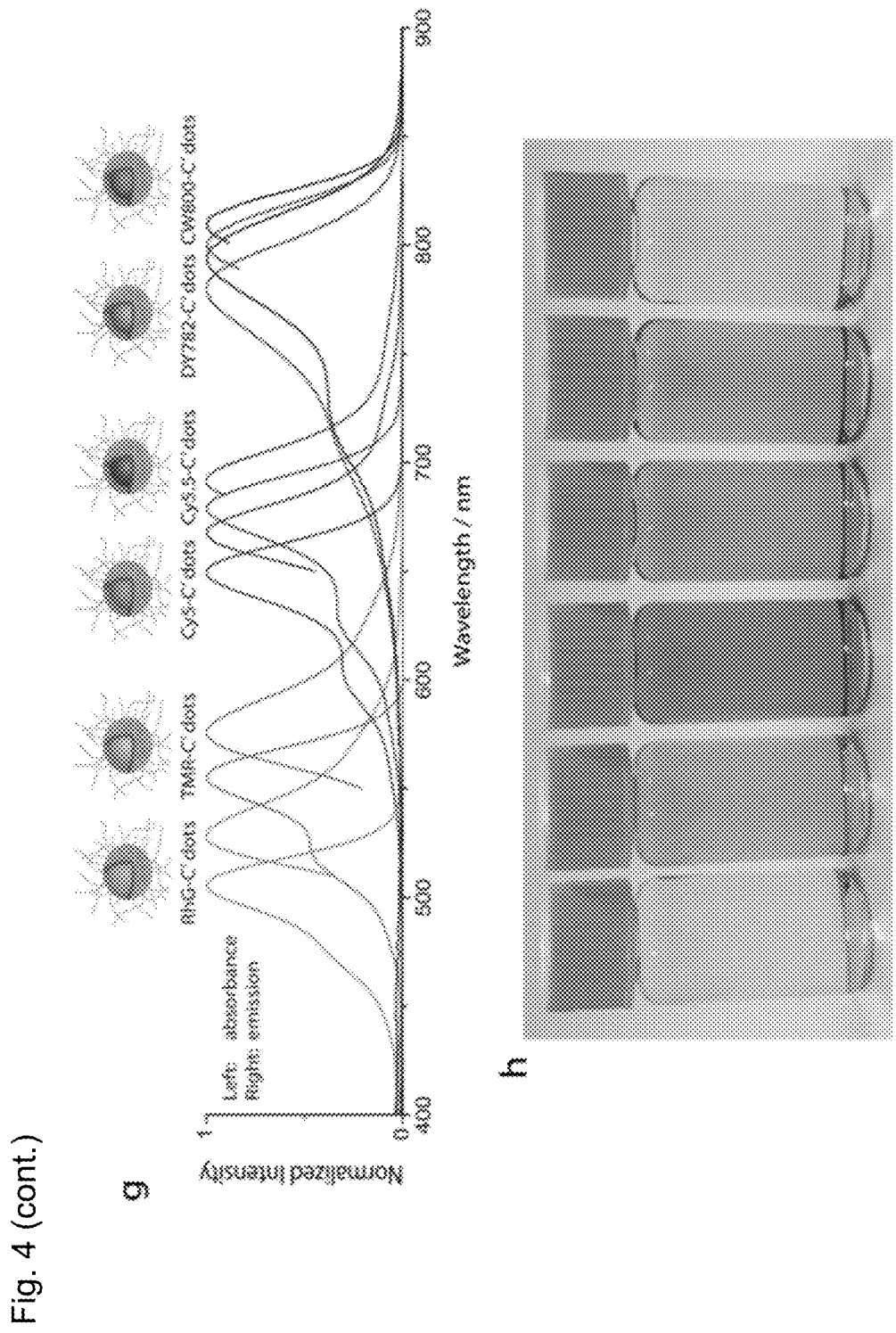

In addition to Cy5 dye other types of fluorophores, including rhodamine green (RhG), tetramethylrhodamine (TMR), Cy5.5, Dyomics 782 (DY782) and IRDye 800CW (CW800), are encapsulated to produce core-shell C' dots of varying colors. Respective steady-state spectra and FCS characterization results are displayed in FIG. 4a-f and results are summarized in Table 4. These C' dots are synthesized following the 4.2 nm sized core protocol plus the addition of a 1 nm thick silica shell. As shown in Table 4, final particle sizes vary between 5.2 nm (DY782) and 6.7 nm (Cy5.5), each particle type containing around 1-2 fluorophores. FIGS. 4g and 4h compare the absorbance/emission spectra and the solution appearance of the different C' dots, respectively. It is interesting to note that the particle synthesis is compatible with different types of fluorophores with optical characteristics all the way from the blue part of the optical spectrum to the NIR. Especially in the 650-800 nm regime, different color NIR C' dots can be synthesized enabling multi-color NIR imaging and NIR multiplexing.

TABLE 4

Comparison of C' dots from different types of fluorophores. Diameter and brightness are measured by FCS while the number of dyes per particle is calculated from steady-state absorbance measurements on different C' dots and particle concentrations as measured by FCS.

|  | Diameter | # of Dyes per Particle | Quantum Enhancement | Brightness to free dye | Abs./Emi. Wavelength |
|---|---|---|---|---|---|
| RhG C' dots | 6.2 nm | 1.8 | 1.4 | 2.6 times | 506/528 nm |
| TMR C' dots | 6.5 nm | 2.0 | 1.7 | 2.2 times | 556/576 nm |
| Cy5 C' dots | 6.1 nm | 1.4 | 1.5 | 2.4 times | 649/668 nm |
| Cy5.5 C' dots | 6.7 nm | 1.5 | 1.5 | 2.4 times | 678/695 nm |
| DY782 C' dots | 5.2 nm | 1.3 | 5.6 | 6.2 times | 780/799 nm |
| CW800 C' dots | 5.5 nm | 1.2 | 1.1 | 1.2 times | 792/808 nm |

3.4. Controlled Fluorescent Silica Nanoparticle Growth with Different Inorganic compositions. Fluorophores with emission spectra moving further out into the NIR typically have larger molar mass and size, therefore requiring more negatively charged sulfate groups on the periphery of their delocalized π-electron systems to generate the desired water solubility, e.g. compare molecular structures of Cy5 and Cy5.5 in FIG. 1. Since silica above its isoelectric point at pH>2.7 is also negatively charged, it can be challenging to covalently encapsulate such highly negatively charged NIR fluorophores into SNPs due to increasing electrostatic repulsive interactions. Here, the aqueous SNP growth solution pH is adjusted to values (pH ~1.5) slightly below the isoelectric point of silica (pH ~2.7). Since under these conditions SNPs would have a low (positive) charge density and therefore particle suspensions in aqueous solutions would be unstable, an aluminum alkoxide is added to the reaction mixture together with the silica source (TMOS). At the low pH, aluminum based reaction intermediates are positively charged (while in-framework aluminum replacing silicon in the network carries a negative charge). From the experimental results, this stabilizes the growing particles enough to prevent aggregation. As shown herein, at the same time the weakly positively charged silica at pH~1.5 provides attractive interactions to negatively charged fluorophores, thereby facilitating their incorporation. Aluminum alkoxides are can be good choice for this purpose, as alumina derived from its alkoxides has already been approved for injection as one of the most common immunization adjuvants. The resulting ultrasmall NIR fluorescent aluminum containing SNPs may therefore also have potential for clinical translation.

Figure 14:
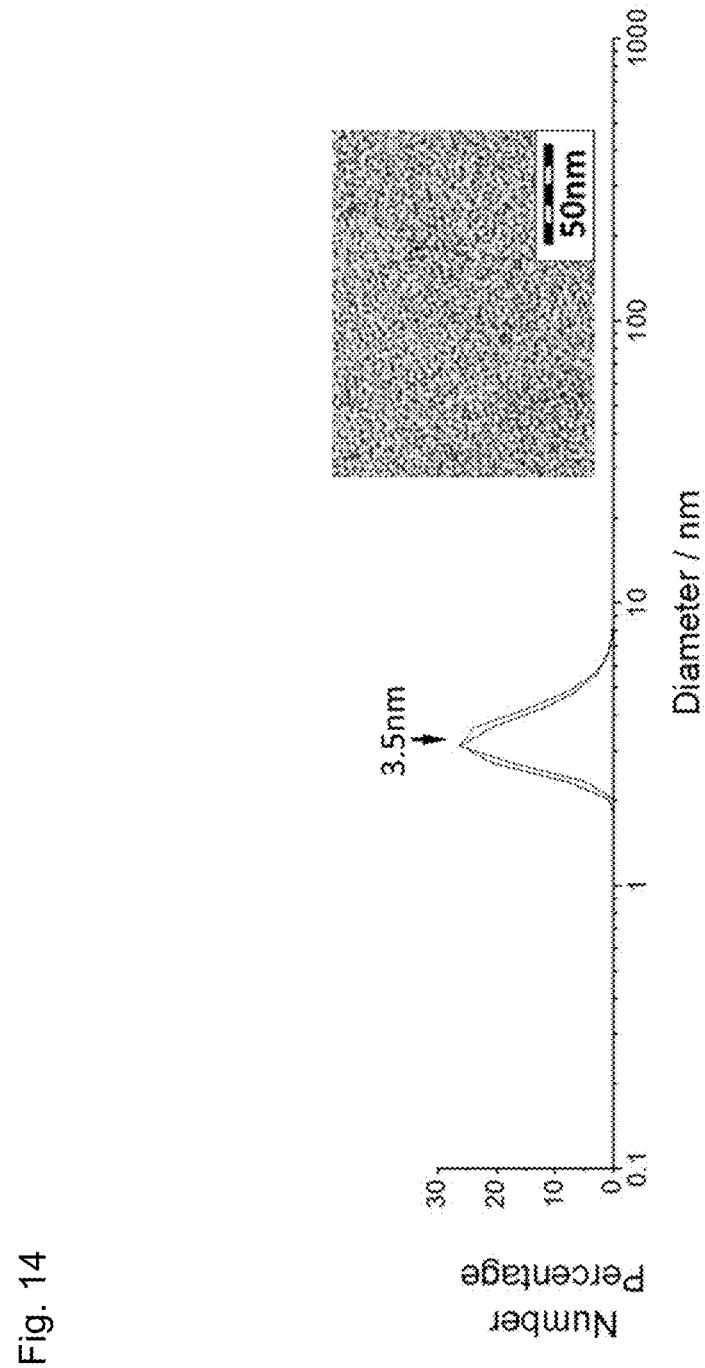
FIG. 14 shows DLS size distribution and TEM of ASNPs with average diameter around 3.5 nm.

In order to incorporate aluminum into SNPs, the solution pH is adjusted to around 1.5 using HCl. An aluminum-tri-sec-butoxide/isopropanol mixture and TMOS (molar ratio around 1:10) are then added simultaneously followed by addition of PEG-silane after 10 minutes of reaction time to terminate particle growth. After adjusting the solution pH back to neutral using ammonium hydroxide, an 80° C. heat treatment is applied to enhance covalent particle PEGylation. As evidenced by a combination of TEM and DLS (FIG. 14), around 3 nm and narrowly size-dispersed NPs can be successfully synthesized in this way.

Figure 5:
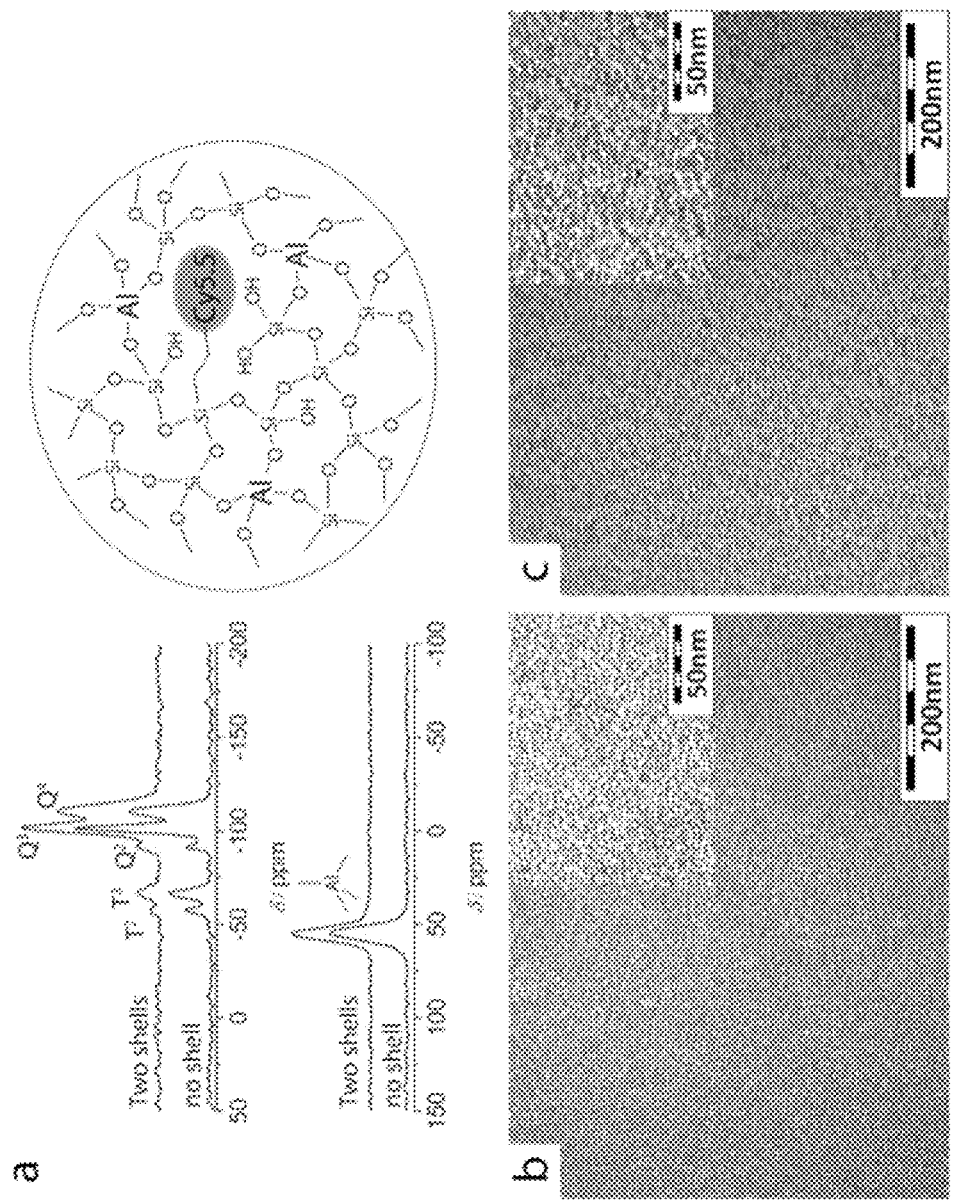
FIG. 5 shows (a) Solid-state $^{29}$Si CP/MAS (top) and $^{27}$Al MAS (bottom) NMR spectra of AlC' dots with and without silica shells; the insert on the right shows a model of the molecular structure of the corresponding aluminosilicate network together with covalently encapsulated NIR Cy5.5 dye. (b) TEM image of core ASNPs. (c) TEM image of core-shell ASNPs. (d) FCS autocorrelation curves and (e) absorbance (matched) and emission spectra of Cy5.5 encapsulating core ASNPs and core-shell AlC' dots compared to free Cy5.5 dye in aqueous solution. (f, g) GPC elution curves obtained from Cy5 (f) and Cy5.5 (g) encapsulating particle batches synthesized under dramatically different pH conditions as compared to conventional C' dots, see description in text. Vertical hatched lines indicate elution times of molar mass standards (in kilo Dalton, kDa) as a guide.
Figure 5:
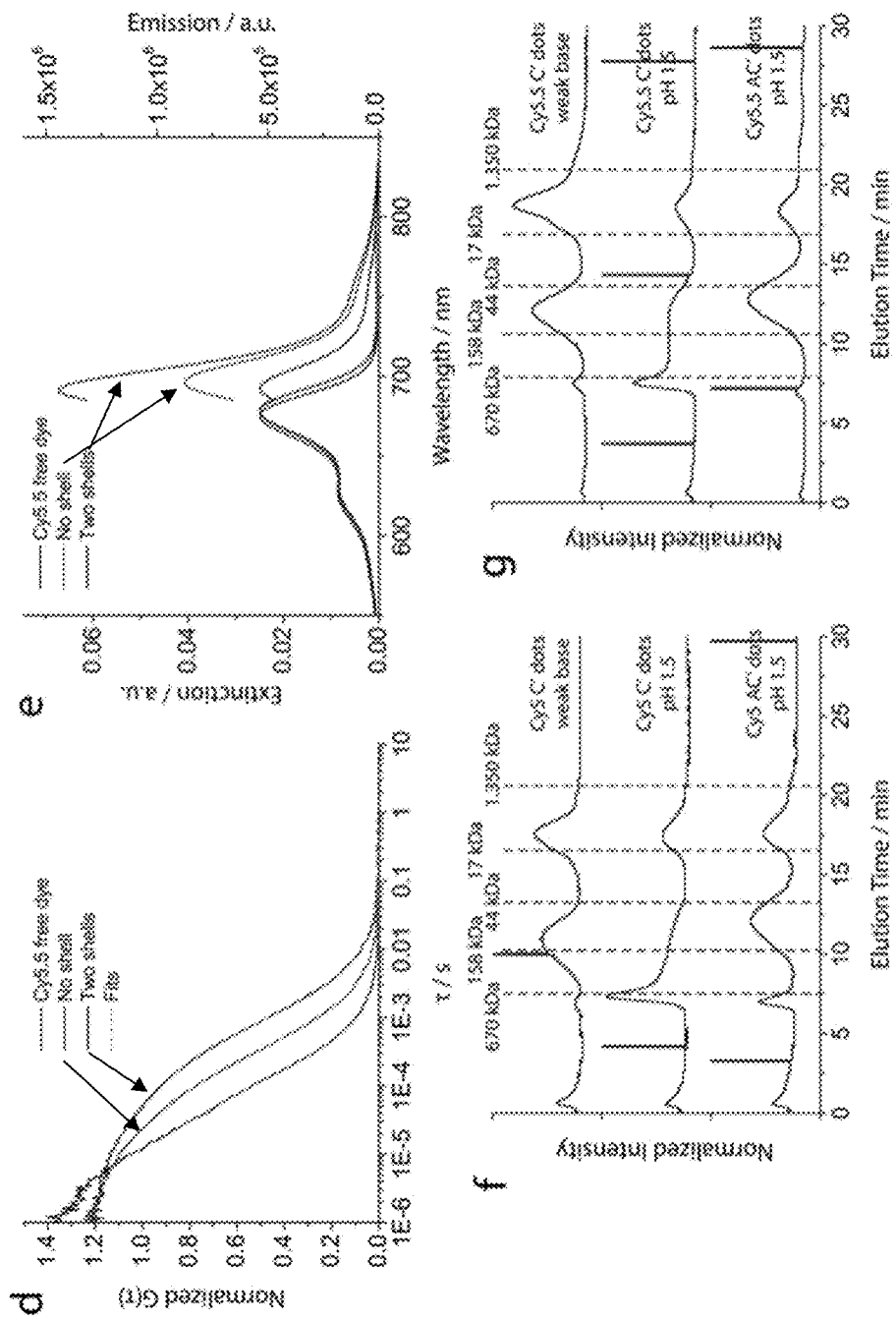

It should be noted that at the strongly acidic conditions used here pure SNPs cannot be generated. Without aluminum composition, silica nanoparticles are not stable at the strong acid condition. To synthesize silica nanoparticles at conditions with pH below the isoelectric point of silica (i.e. pH 2.7), which is desired for the encapsulation of highly negatively charged near-IR dyes, aluminum has to be used for particle stability. As a result of the proximity of the solution pH to the isoelectric point of silica at 2.7, the surface charge density of SNPs is not high enough to electrostatically stabilize particles and consequently particle aggregation occurs. In contrast, since the hydrolysis product of aluminum alkoxide at acidic conditions is strongly positively charged, $[Al(OH_2)_6]^{3+}$, and in-framework aluminum is negatively charged, we hypothesize that as aluminum co-condenses with silica it may add enough charge to the growing particles so that electrostatic repulsive interactions prevent uncontrolled particle aggregation. Other mechanisms also are possible. The diminished negative charge density of growing particles in this synthesis protocol may also help to reduce the repulsion to negatively charged NIR fluorophores thereby facilitating their encapsulation into the NPs. In order to prove this principle, ultrasmall <10 nm Cy5.5 labeled NPs were synthesized by adding dye conjugated silane into the reaction mixture. The successful incorporation of aluminum into silica of these particles is checked first by solid-state NMR. The 29Si NMR spectrum in FIG. 5a evidences T and Q groups in agreement with previous studies demonstrating a silica-based particle matrix (Q groups) and PEG-silane condensation on the particle surface (T groups). The 27Al NMR spectrum only shows one sharp peak at around −56 ppm indicating four-fold coordinated in-framework aluminum. An illustration of the molecular structure of the corresponding aluminosilicate network together with covalently encapsulated NIR dye is also shown in FIG. 5a. Particle formation was further confirmed by a combination of TEM as well as FCS (FIGS. 5b and 5d) and particle size as determined by FCS is 4.2 nm. Unaltered shapes of absorbance and emission spectra suggest survival of the Cy5.5 fluorophore despite the strongly acidic synthesis conditions (FIG. 5e).

In order to prove more quantitatively that this synthesis protocol enhances the encapsulation of highly negatively charged fluorophores, the aluminum containing Cy5.5 labeled SNPs, as well as the results of various control reactions, are subjected to GPC characterization immediately after synthesis and before any cleaning step. As shown in FIGS. 5f and 5g, the elugrams of conventional Cy5 and Cy5.5 labeled SNPs synthesized using weak base conditions have three main peaks.

In order to assign the peaks in the GPC elugram, a Cy5 doped PEGylated SNP synthesis batch is sorted into different factions by GPC and each faction is then subjected to FCS characterization. The average concentration of particles, particle brightness and particle diameter of each faction are shown in the upper three graphs in FIG. 15. The GPC peak at around 18 minutes corresponds to objects in solution with a diameter around 1-2 nm, which in turn corresponds well to the size of free Cy5-silane conjugates or small self-condensed Cy5-silane conjugate clusters. In addition, the brightness per object corresponding to the 18 minute peak is close to the brightness of a single Cy5 fluorophore. This peak may be from free Cy5-silane dye conjugate or Cy5 conjugate clusters which are not encapsulated into particles. The main GPC peak at around 12 minutes corresponds to objects in solution with a diameter of around 6 nm and brightness levels more than two times the brightness of free Cy5 fluorophore. Both parameters correspond well to what is expected for the targeted fluorescent Cy5 encapsulating SNPs. The main peak at around 12 minute may be from the desired C' dots. The GPC peak at around 6-7 minutes corresponds to objects in solution with a fairly big diameter of up to 20 nm. Interestingly, the brightness per object corresponding to this peak is similar to that of a single fluorescent SNP. This peak should therefore not be assigned to objects coming purely from SNP aggregation. Furthermore, although a well-defined small peak can be observed in the GPC equipped with a 275 nm detector, this peak corresponds to objects in solution with very low concentration as observed by FCS. This suggests that the larger objects (up to 20 nm) in solution giving rise to this peak with small absorbance at 275 nm and low fluorescence may come from impurities of the chemicals used in the synthesis, e.g. PEG-silane, but may not have much to do with the particle synthesis reaction.

Figure 15:
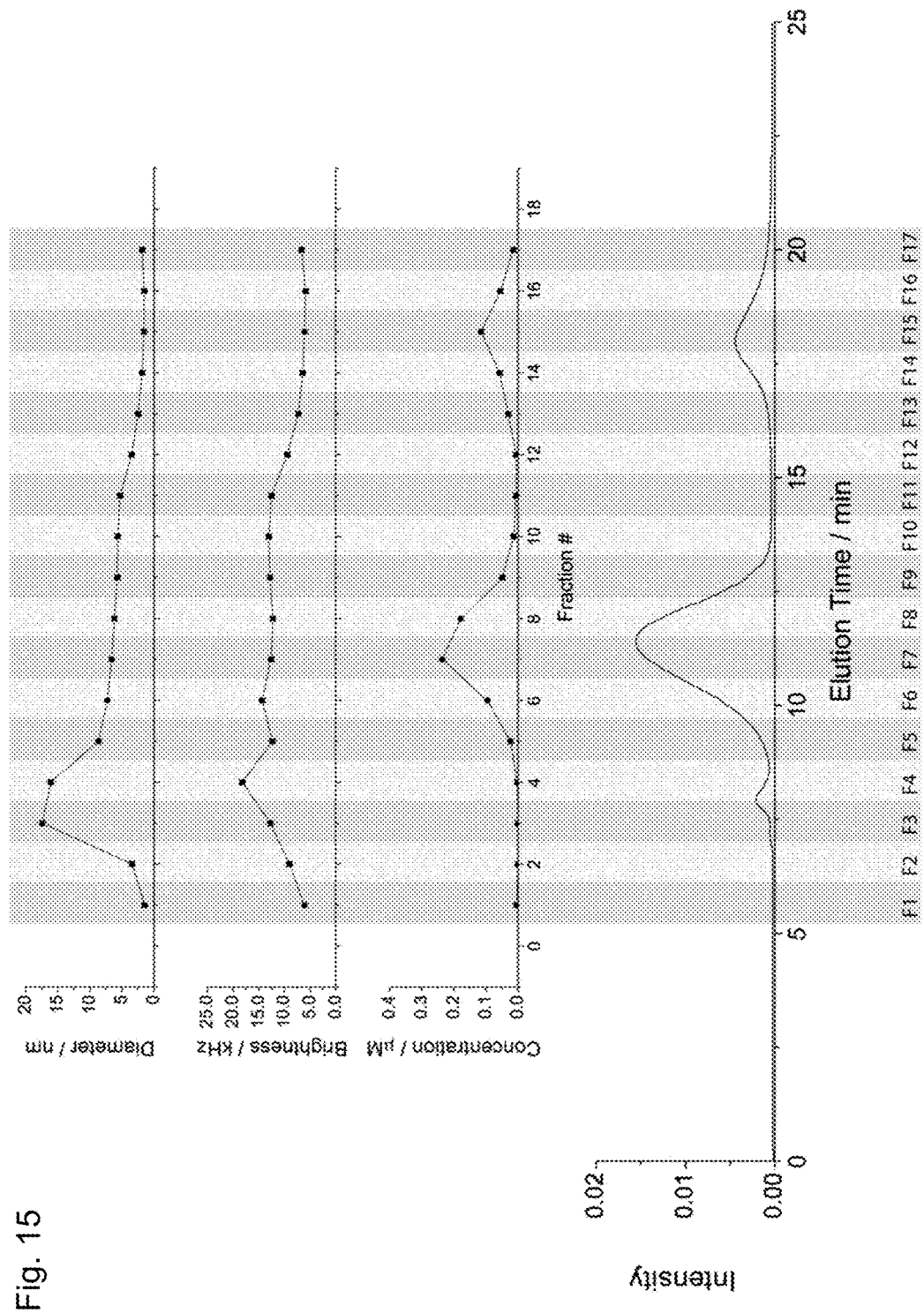
FIG. 15 shows a GPC elugram of as-synthesized Cy5 doped PEGylated SNPs (Cy5-C' dot, no shell, bottom graph) and related FCS characterization results of different fractions (upper three graphs).

As indicated in FIG. 15, the peak at around 7 minutes stems from larger aggregates, which usually will be filtered away via cleaning. The peak at around 18 minutes is from unreacted dye molecules, which will be washed away through dialysis. The peak at around 12 minutes is the main particle peak. By comparing the peak area of unreacted fluorophores and particles, the percentage of encapsulated fluorophore can be estimated. First of all, the data reveals that the degree of encapsulation greatly depends on fluorophore, and with it on the number of charges per dye. Around 60% silane-conjugated Cy5 dye, which contains one negative charge, is encapsulated into particles at weak base conditions, while this percentage decreases to only ~40% for Cy5.5, which contains three negative charges per molecule. As the reaction pH is decreased to 1.5, no free particle peak is observed for either Cy5 or Cy5.5, whereas the elugrams indicate strong particle aggregation most likely due to loss of particle surface charge. In contrast, as the aluminum alkoxide is submitted to the reaction mixture together with TMOS at low pH, for both dyes a clear particle peak reemerges in the elugrams, while the aggregation peak is strongly suppressed. Interestingly, under the strongly acidic synthesis conditions the encapsulation efficiency as revealed by the areas under the respective peaks for both dyes increases. The effect is stronger for Cy5.5 where the efficiency increases from ~40% to >70%.

TABLE 5

Comparison of Cy5.5 encapsulating aluminosilicate nanoparticles. Diameter and brightness are measured by FCS while the number of dyes per particle is calculated from steady-state absorbance measurements on different C' dots and particle concentrations as measured by FCS.

| | Diameter | # of Dyes per Particle | Quantum Enhancement | Particle brightness relative to free dye |
|---|---|---|---|---|
| Cy5.5 | 1.3 nm | 1.0 | — | — |
| Cy5.5 core | 4.2 nm | 1.4 | 1.7 | 2.1 times |
| Cy5.5 core-shell | 7.6 nm | 1.3 | 2.6 | 3.0 times |

Two additional silica shells are added to the Cy5.5 encapsulated aluminosilicate core before PEGylation to further enhance the fluorophore quantum efficiency (illustration shown in FIG. 1). 29Si and 27Al solid-state NMR spectra of the resulting aluminum containing core-shell nanoparticles (FIG. 5a) show consistent characteristics as compared to the particles without shell, corroborating the presence of four-fold coordinated in-framework aluminum. Considering that the T groups in the 29Si spectrum originate from PEG-silane condensing onto the particle surface, the decrease of the T group intensity relative to Q groups in the 29Si spectrum after shell addition is consistent with a decreased surface/volume ratio, which suggests successful silica shell deposition. The average diameter of the core-shell Aluminum containing dots, obtained from TEM (FIG. 5c) is around 5 nm (hard particle diameter only), while FCS (FIG. 5d) measures 7.6 nm (hard particle plus soft PEG shell plus hydration layer) further suggesting the successful shell addition to the core particle of 4.2 nm (Table 5 As measured by steady-state absorption and FCS concentration analysis, these dots have a quantum enhancement over free dye of 2.6, which is much higher than the value of 1.7 obtained for the core only (FIG. 5e, Table 5). As shown in Table 5, this is confirmed by FCS suggesting that the core-shell particles are around 1.5 times brighter than the core particles. Furthermore, the highest quantum enhancements of plain Cy5.5 C' dots (i.e. without addition of aluminum alkoxide) that were synthesized is around 1.7-2.2, even with several nm thick silica shells. This high quantum enhancement over free dye of 2.6 may be the result of increased matrix rigidity surrounding the dye since incorporation of aluminum into the silica network is known to enhance its rigidity. Considering the quantum yield of Cy5.5 free dye in water is about 0.3, the observed enhancement of 2.6 is equivalent to a quantum yield of encapsulated dye of around 0.8, which is quite high and starting to approach the theoretical brightness limit.

In order to distinguish these aluminum containing fluorescent SNPs synthesized in water from C' dots, they will be referred to as AlC' dots. Finally, as a result of the fast reaction rate of the aluminum alkoxide the final core-shell AlC' dot surface should be indistinguishable from that of conventional C' dots as the aluminum is expected to reside only in the core while the shells are made of plain silica covalently decorated with PEG chains as in the case of the C' dots.

Figure 6:
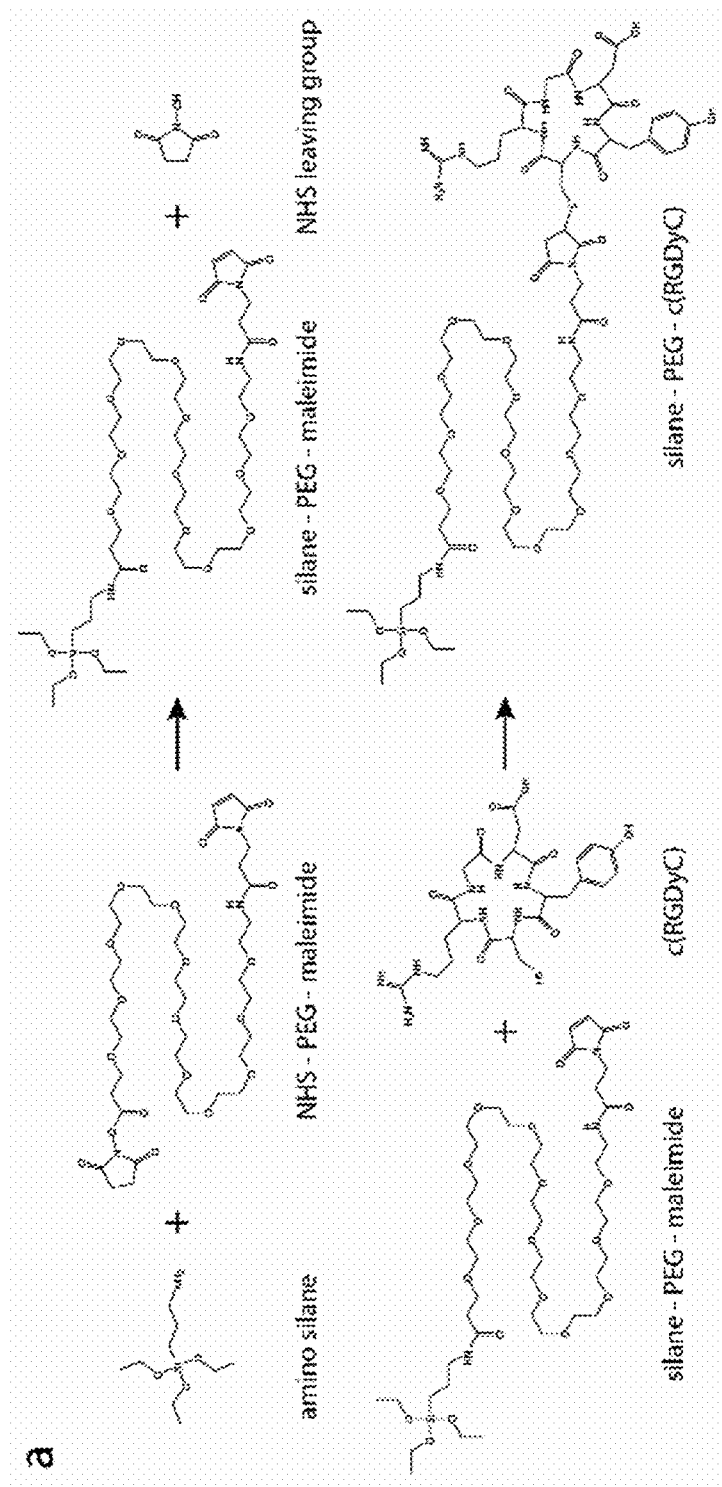
FIG. 6 shows (a) Conjugation chemistry of c (RGDyC) functionalized PEG-silane. (b) Absorbance spectra comparing free c (RGDyC) peptide, free Cy5 dye and Cy5-C' dots (no silica shell) with/without c (RGDyC) surface functionalization suggesting successful c (RGDyC) surface modification. (c) Absorbance spectra comparing free c (RGDyC) peptide and different types of c (RGDyC) surface functionalized C' dots suggesting success of nanoparticle-PEG-surface functionalization with ligands is independent of particle architecture (i.e. with or without extra silica shells), types of fluorophores encapsulated, or particle composition (i.e. C' dots versus AlC' dots).
Figure 6:
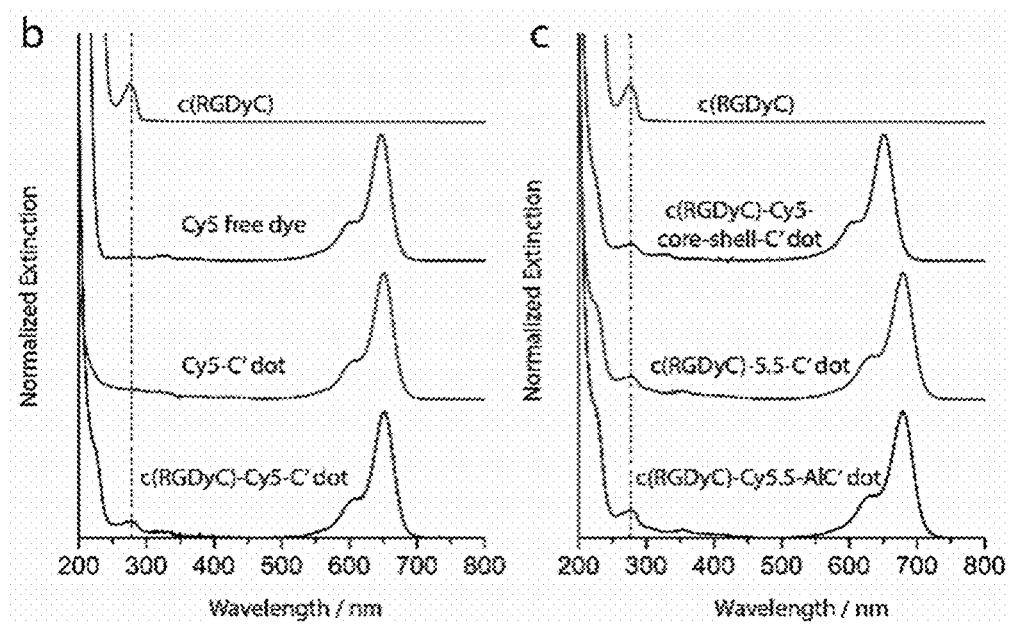
Figure 16:
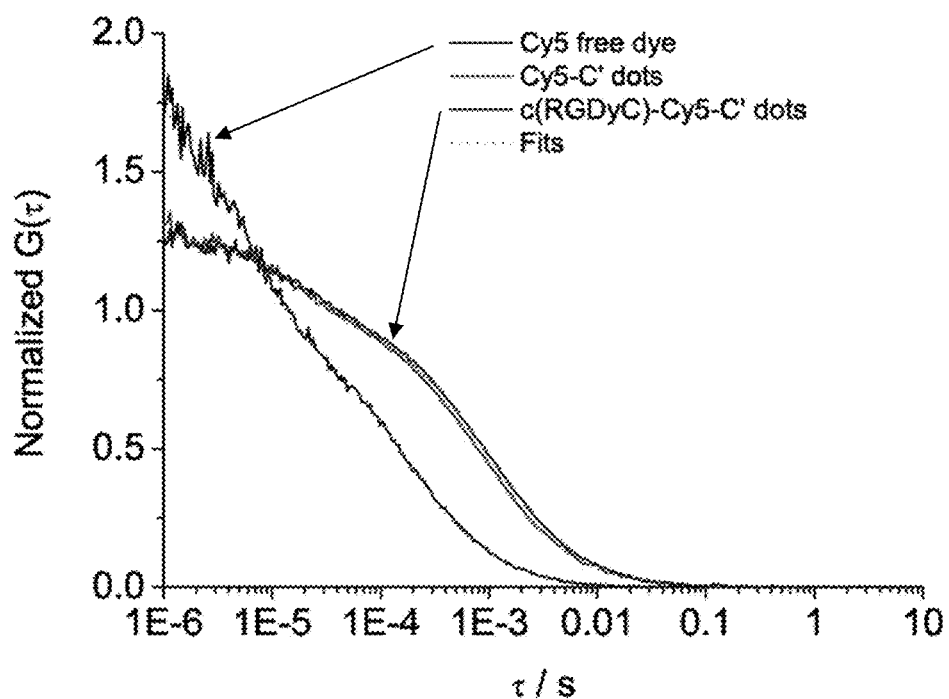
FIG. 16 shows a comparison of FCS measured autocorrelation curves of free Cy5 dye, Cy5-C' dots (core only), and c (RGDyC) functionalized Cy5-C' dots (c (RGDyC)-Cy5-C' dots).

3.5. Ligand Functionalized Fluorescent Silica Nanoparticles. Heterobifunctional PEGs are employed to introduce easily accessible ligands onto the PEGylated particle surface of fluorescent SNPs and core-shell SNPS, as well as their aluminum containing analogues. This produces ligand functionalized<10 nm NIR fluorescent nanoprobes e.g. for preclinical and clinical use in diagnostic and therapeutic applications. Ligands interesting for such applications include, but are not limited to, peptides, antibody fragments, various DNA and RNA segments (e.g. siRNA), therapeutic molecules including drugs as well as radioisotopes and their respective chelating moieties, and combinations thereof. Here, proof-of-principle is demonstrated using $\alpha_v\beta_3$ integrin-targeting cyclic (arginine-glycine-aspartic acid, tyrosine-cysteine) peptides, c (RGDyC), containing a tyrosine (Y) residue to bind a radioisotope, e.g. 124I, and a cysteine (C) residue to bind to the maleimido-functionalized heterobifunctional PEGs. As displayed in FIG. 6a, to that end heterobifunctional PEGs with NHS ester and maleimide groups at their chain ends (NHS-PEG-mal with molar mass around 800 g/mole) are first conjugated with amino silane through reaction of the amine with the NHS ester group. In a second step the resulting silane-PEG-maleimide is further conjugated with c (RGDyC) through thiol maleimide reaction to produce c (RGDyC) functionalized PEG-silane (c (RGDyC)-PEG-silane). The heterobifunctional PEG is chosen to be a bit longer as compared to the PEG-silane (800 g/mole as compared to 500 g/mole, respectively). This ensures that the surface ligands are sticking out a bit beyond the surface of the PEG-silane coating and are therefore easily accessible (see also models in FIG. 7). The final c (RGDyC)-PEG-silane is added into the nano-dot synthesis solution together with monofunctional PEG-silane in the PEGylation step. As a result, the surface of the synthesized nano-dots is covalently covered by both the common PEG chains and the longer c (RGDyC) functionalized PEG chains (FIG. 1). FIG. 6b compares the absorbance spectra of free c (RGDyC) peptide, free Cy5 dye, and Cy5 encapsulated C' dot cores (Cy5-C' dots, no silica shell) with/without c (RGDyC) surface functionalization. The c (RGDyC) peptide has an absorbance peak at 275 nm from the tyrosine residue, while neither the Cy5 free dye nor the Cy5-C' dots show detectable signals in this wavelength range. This absorbance peak can thus be used to verify successful particle surface functionalization. Indeed, the c (RGDyC) functionalized PEG-Cy5-C' dots (c (RGDyC)-PEG-Cy5-C' dots) show an absorbance peak at around 275 nm in addition to the 650 nm Cy5 absorbance peak. Furthermore, as shown in FIG. 16, the FCS measured autocorrelation curve of c (RGDyC)-PEG-Cy5-C' dots slightly shifts to the right compared to the dots without c (RGDyC) surface modification, indicating a ~1 nm particle size increase after attaching c (RGDyC) ligands to the particle surface (Table 6). These data suggest the c (RGDyC) peptides have been successfully attached to the particle surface. Combining the absorbance and FCS characterizations, the number of c (RGDyC) ligands per C' dot can be calculated. As shown in Table 6, from this synthesis batch on average around 16 c (RGDyC) peptides are attached to a single Cy5-C' dot (no silica shell). End ligand numbers can be varied via the synthesis conditions, e.g. by changing the ratio of ligand-bearing and plain PEG-silane added in the particle synthesis step.

TABLE 6

Characterization of various c(RGDyC) functionalized C' dots,
including fluorescent SNPs (C' dots, core only), core-shell
SNPS (core-shell-C'dot), and their aluminum containing analogues.

| | FCS Diameter | # of Dyes per Particle | # of c(RGDyC) per Particle |
|---|---|---|---|
| Cy5 | 1.3 nm | — | — |
| Cy5-C' dots | 5.4 nm | 1.8 | — |
| c(RGDyC)-Cy5-C' dots | 6.5 nm | 1.8 | 16 |
| c(RGDyC)-core-shell-Cy5-C' dots | 7.4 nm | 1.8 | 22 |
| c(RGDyC)-Cy5.5-C' dots | 6.2 nm | 1.7 | 19 |
| c(RGDyC)-Cy5.5-AlC' dots | 6.1 nm | 1.4 | 12 |

By combining FCS and optical absorbance measurements, the number of c (RGDyC) ligands per C' dot can be estimated in a similar way as the calculation of the number of dyes per C' dot. For example, the height of the 275 nm c (RGDyC) peak in the c (RGDyC)-C' dot optical spectrum (FIG. 6b) can be estimated through subtracting from it the absorbance spectrum background obtained from non-c (RGDyC) ligand containing C' dots. Then, by dividing the resulting c (RGDyC) peak height by the extinction coefficient of tyrosine, e.g. around 1400 $M^{-1}$ $cm^{-1}$, the concentration of total number of c (RGDyC) ligands present in the solution can be calculated. Meanwhile, the concentration of C' dots in solution can be measured by FCS. Finally, by taking the ratio of c (RGDyC) concentration to C' dot particle concentration the number of c (RGDyC) ligands per particle can be estimated. The results suggest that the number of c (RGDyC) ligands on the various C' dots synthesized in this study is between 12 and 22 (see Table 6).

In order to prove that this surface modification methodology can be applied to other particle platforms in the C' dot family, c (RGDyC) peptides are attached to types of C' dots under similar reaction conditions. In detail, these include C' dots with additional silica shells, with different types of fluorophore (Cy5.5 vs. Cy5) and with different composition (AlC' dots vs. C' dots). As displayed in FIG. 6c, all these synthesized particles show the absorbance peak at around 275 nm characteristic for c (RGDyC) indicating successful c (RGDyC) surface modification in all cases. The number of c (RGDyC) peptides per particle as derived from these optical measurements combined with FCS results slightly varies from 12 to 22 (Table 6).

Considering that each 6 nm C' dot has roughly around 100 PEG chains on the surface according to thermogravimetric analysis (TGA; see FIG. 17), a number that changes with particle size, it can be estimated that one out of 5-10 PEG chains is functionalized with a c (RGDyC) ligand. Besides absolute ligand number, ligand density is another parameter that is expected to control biological response, and can be tuned via the synthesis parameters discussed in this study. The surface density of monofunctional PEG chains and c (RGDyC)-functionalized PEG chains of the synthesized ~7 nm C' dot are estimated to be roughly 1.7/$nm^2$ and 0.2/$nm^2$, respectively. For the plain PEG chains this is equivalent to an area per PEG-silane head group of around 0.6 $nm^2$. For comparison it is interesting to note that the overall surface density of PEG chains on a high curvature C' dot surface is very close to the reported ligand densities of shorter functional alkyl-silane monolayers on planar silica which is between 1.2/$nm^2$ and 2.2/$nm^2$, or between 0.83 $nm^2$ and 0.45 $nm^2$ when expressed as area per head group.

Figure 17:
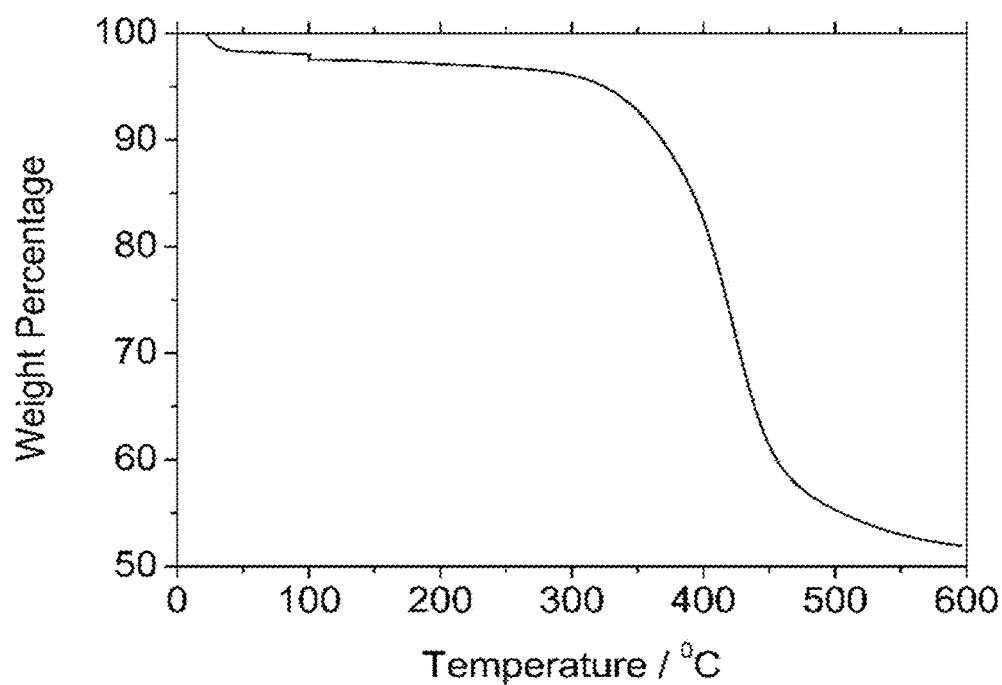
FIG. 17 shows a TGA curve for a 6 nm (measured by DLS) blank non-fluorescent PEGylated SNP (without fluorophore encapsulation).

A TGA curve for a 6 nm blank non-fluorescent PEGylated SNP (without fluorophore encapsulation) is displayed in FIG. 17. The 6 nm average size is the hydrodynamic diameter as measured by DLS. The weight loss up to temperatures of 600° C. indicates the presence of organic content in the particle sample. Since this sample synthesis did not include encapsulation steps of a fluorescent dye, the only organic content of the particle stems from the PEG chains on the particle surface. The TGA curve becomes flat at around 600° C. suggesting most of the organic content has been burned off leaving inorganic silica as the remaining constituent. From this data it can then be estimated that the weight ratio between silica and PEGs is around 52%:48%. Considering that the 6 nm hydrodynamic diameter PEGylated SNPs have a pure silica core of ~4 nm and a ~1-2 nm PEG layer, the number of PEG chains per particle can be estimated by assuming a silica density of about 1.9-2.2 g/$cm^3$. Results suggest for this simple SNP there are around 80-100 PEG chains on the particle surface. This translates to a PEG density on the particle surface of about 1.7 chains/$nm^2$, which is equivalent to an area per PEG-silane head group of around 0.6 $nm^2$. The number of PEGs per particle goes up as particle size increases. Comparing this surface density of PEGs to the number of c (RGDyC) per particle, it can be estimated that on the surface of c (RGDyC)-PEG-C' dots synthesized herein, there is roughly one c (RGDyC)-labeled PEG chain among every 5-10 unfunctionalized PEG chains.

Figure 7:
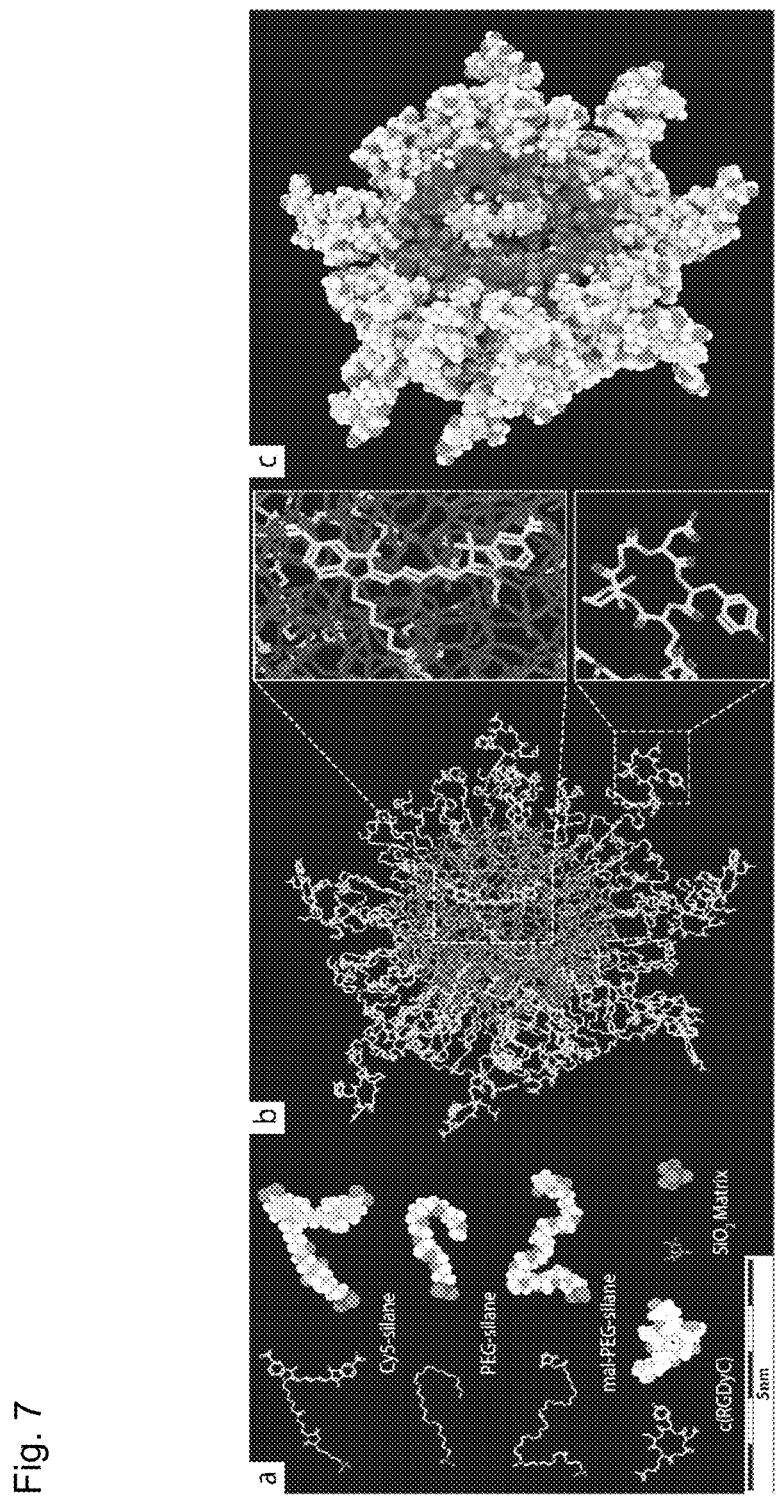
FIG. 7 shows a molecular-graphics rendering of Cy5 fluorophore, PEG-silane, maleimide-functionalized PEG-silane, c (RGDyC) peptide, $SiO_2$ matrix (a) and a c (RGDyC)-PEG-Cy5-C' dot (b and c). The C' dot model consists of a ~3 nm silica core which encapsulates one Cy5 fluoro-phore, a ~1 nm silica shell, a ~1.5 nm PEG layer and 16 easily accessible c (RGDyC) ligands. The molecular models are displayed in different modes for visualization including the molecular framework without hydrogen (b) and the sphere-based molecular model with realistic atomic dimensions (c).

3.6. Molecular Models of Ligand Functionalized PEGylated Fluorescent Core-Shell Silica Nanoparticles. Based on the full analysis results, realistically scaled molecular models of a ligand functionalized Cy5 encapsulating PEGylated core-shell C' dot with c (RGDyC) surface modification (i.e. of a c (RGDyC)-PEG-Cy5-C' dot) are displayed in FIG. 7. For size comparison, from top to bottom the left side (FIG. 7a) shows models of individual components constituting this particle: Cy5 dye, PEG-silane (around 500 g/mole), maleimide-functionalized (i.e. heterobifunctional) PEG-silane (around 800 g/mole), c (RGDyC) peptide, as well as silica. The models in FIGS. 7b and 7c represent a cut through a C' dot with a ~3 nm diameter silica core encapsulating one Cy5 fluorophore (FIG. 7b, top inset), a ~0.5 nm thick silica shell, a ~1.5 nm thick PEG layer, and 16 c (RGDyC) ligands (FIG. 7b, bottom inset) at the end of heterobifunctional PEGs that are a bit longer than the PEG-silanes. According to an amorphous silica density around 1.9-2.2 g/$cm^3$, this silica nanoparticle consists of about 800 $SiO_2$ units and about 100 PEG chains on the particle surface. The overall particle size is around 7.5 nm and the overall particle molar mass is about 110 kDa. As shown in FIG. 7a, the length of a Cy5 fluorophore is between 2 and 3 nm although its hydrodynamic diameter as measured by FCS is only slightly larger than 1 nm (Table 3). Based on FIG. 7, it can be concluded that a location of the covalently bonded Cy5 fluorophore exactly inside the 3 nm silica core is unlikely given the stochastic nature of the encapsulation process and the electrostatic repulsion between Cy5 and negatively charged deprotonated silica surface hydroxyl groups. In order to be fully covered/encapsulated by silica, rather an additional silica shell is necessary consistent with the fact that extra silica shells result in further quantum yield enhancements (FIGS. 3g and 3i). There are only about 10 $SiO_2$ structural units across the silica core-shell part of the C' dot further emphasizing the near-molecular or macromolecular size of these nanoparticles.

In this example an aqueous synthesis methodology for the generation of narrowly size-dispersed PEGylated SNPs with size control below 1 nm is presented (e.g., at the level of single atom layers). Different types of fluorophores including NIR emitting dyes can be encapsulated into the particles to produce fluorescent probes whose brightness can be further enhanced via addition of extra silica shells before PEGylation. This methodology further enables synthesis of <10 nm sized fluorescent SNPs with other compositions. In particular the addition of an aluminum sol-gel precursor leads to aluminum containing fluorescent core and core-shell nanoparticles, for which not only the encapsulation efficiency of highly negatively charged NIR fluorophores is enhanced relative to the silica particles, but also the quantum enhancement of individual fluorophores is starting to approach the theoretical brightness limit. Finally, heterobifunctional PEGs can be employed to introduce easily accessible ligands onto the PEGylated particle surface of fluorescent SNPs and core-shell SNPS, as well as their aluminum containing analogues, producing <10 nm NIR fluorescent nanoprobes for preclinical and clinical use in diagnostic and therapeutic applications. NP structure correlations as described here may also help improve fundamental understanding of the mechanisms of early growth states of SNPs.

Although the present disclosure has been described with respect to one or more particular embodiments and/or examples, it will be understood that other embodiments and/or examples of the present disclosure may be made without departing from the scope of the present disclosure.

What is claimed is:

1. A method of making a Cornell prime dot (C' dot), comprising:
    forming a reaction mixture comprising water, tetramethyl orthosilicate, and a fluorescent dye precursor, wherein the reaction mixture does not contain an organic solvent at 10% or greater, other than a polar aprotic solvent;
    holding the reaction mixture for a period of time; and
    adding to the reaction mixture a PEG-silane conjugate, thereby forming a C' dot.

2. The method of claim 1, wherein the pH of the reaction mixture is 6 to 9.

3. The method of claim 1, further comprising a step of purifying the C' dot.

4. The method of claim 3, wherein the step of purifying comprises gel permeation chromatography (GPC).

5. The method of claim 3, wherein the step of purifying comprises filtration.

6. The method of claim 1, wherein the method comprises encapsulating 1 to 7 fluorescent dye molecules in the C' dot.

7. The method of claim 1, wherein the dye precursor comprises a Cy5 or Cy5.5 fluorophore.

8. The method of claim 1, further comprising conjugating a ligand to the C' dot.

9. The method of claim 8, wherein the ligand comprises a therapeutic agent.

10. The method of claim 9, wherein the therapeutic agent is a chemotherapeutic agent.

11. The method of claim 8, wherein the ligand comprises a drug-linker conjugate.

12. The method of claim 11, wherein the linker can be cleaved by enzyme or acid in a tumor for drug release.

13. The method of claim 8, wherein the ligand has a specific binding affinity for a tumor.

14. The method of claim 1, further comprising conjugating a reactive group to the C' dot.

15. The method of claim 1, wherein the C' dot has a diameter of 2 to 15 nm.

16. The method of claim 1, wherein a plurality of C' dots are formed.

17. The method of claim 16, wherein the diameters of C' dots in the plurality vary by no more than 1 nm.

* * * * *